United States Patent [19]

Theofilopoulos et al.

[11] Patent Number: 4,960,712
[45] Date of Patent: Oct. 2, 1990

[54] SYSTEM AND METHOD FOR COMPLEMENT PATHWAY ANALYSIS

[75] Inventors: Argyrios N. Theofilopoulos; Frank J. Dixon, both of La Jolla; Maria-Teresa Aguado-Celada, Encinitas, all of Calif.

[73] Assignee: Scripps Clinic and Research Foundation, La Jolla, Calif.

[21] Appl. No.: 213,312

[22] Filed: Jun. 30, 1988

Related U.S. Application Data

[63] Continuation of Ser. No. 552,158, Nov. 15, 1983.

[51] Int. Cl.$^5$ ............................................ G01N 33/566
[52] U.S. Cl. .................................... 436/501; 435/7; 436/507; 436/512; 436/536; 436/539; 436/548; 436/809; 436/821
[58] Field of Search ............... 436/552, 158, 501, 507, 436/539, 548, 808, 821, 512, 536, 804; 435/7

[56] References Cited

U.S. PATENT DOCUMENTS 4,342,566  8/1982  Theofilopoulos et al.
4,642,284  2/1987  Cooper et al. .................. 436/540 X

OTHER PUBLICATIONS

Nydegger and Davis, "Soluble Immune Complexes in Human Disease" in *Critical Reviews in Clinical Laboratory Sciences*, Batsakis and Savory eds., CRC Press, Inc. Boca Raton, Florida pp. 123–170 (1980).
Lachmann, P. J. et al. J. Exp. Med. 156:205–216 (1982).
Ross, G. D. et al., J. Immunology 129:2051–2060 (1982).
Pussell et al., *Lancet*, Aug. 12, 1978, pp. 359–365.
Lachmann et al., *Immunology Today*, Aug. 1981, p. 144.
Theofilopoulos et al., *Advances in Immunology*, 28:89–220 (1979).
Pangburn et al., *J. Immunology*, 124:977–982 (1980).
Wilson et al., *N. Engl. J. Med.*, 307:981–986 (1982).
Medof, *J. Exp. Med.*, 156:1739–1754 (Dec. 1982).
Polhill et al., *J. Immunology*, 121:363–370 (1978).

Primary Examiner—Amelia B. Yarbrough
Assistant Examiner—Mindy B. Fleisher
Attorney, Agent, or Firm—Dressler, Goldsmith, Shore, Sutker & Milnamow

[57] ABSTRACT

The present invention relates to systems and methods used to assay for particular complement component fragments. The invention can be used to determine the amount of a particular complement component fragment in a sample. The fragment can be fluid phase or bound to an immune complex. Generally, specific binding agents, such as antibodies, directed to the complement component fragments and immune complexes are used in the assay.

28 Claims, 22 Drawing Sheets

Mc9 (ANTI-C3g) ANTIBODY BINDING

TOTAL INPUT = 1000 ng

SYSTEM AND METHOD FOR COMPLEMENT PATHWAY ANALYSIS

This is a continuation, of application Ser. No. 552,158, filed Nov. 15, 1983.

TECHNICAL FIELD OF THE INVENTION

The present invention relates to the detection and measurement of complement pathway components.

BACKGROUND OF THE INVENTION

The complement system is a complex group of proteins in body fluids that, working together with antibodies or other factors, play an important role as mediators of immune, allergic, immunochemical and immunopathological reactions. Activation of the complement system can result in a wide range of reactions such as lysis of various kinds of cells, bacteria and protozoa, inactivation of viruses, and the direct mediation of inflammatory processes. Through the hormone-like activity of several of its components, the complement system can recruit and enlist the participation of other humoral and cellular effector systems. These in turn can induce directed migration of leukocytes, trigger histamine release from mast cells, and stimulate the release of lysosomal constituents from phagocytes.

The complement system consists of at least twenty distinct plasma proteins capable of interacting with each other, with antibodies, and with cell membranes. Many of these proteins when activated combine with some of the other proteins to form enzymes to cleave and activate still other proteins in the system. The sequential activation of these proteins follows two main pathways; the classical pathway and the alternative pathway. Both pathways use a common terminal trunk which leads to cell lysis or virus inactivation.

The classical pathway can be activated by antigen-antibody complexes, aggregated immunoglobulins and non-immunological substances such as DNA and trypsin-like enzymes. The classical pathway of activation involves, successively, four components denominated C1, C4, C2 and C3. These components can be grouped into two functional units: C1 or recognition unit; and C4, C2, and C3 or activation unit. Five additional components denominated C5, C6, C7, C8, and C9 define the membrane attack unit forming the terminal-truck common to both pathways In the classical pathway, C1 is activated such as by attachment to an immunoglobulin, and through a series of reactions, produces an activated $\overline{C1s}$ from a constituent of C1. A bar over the term for a complement factor denotes an active enzyme. Activated $\overline{C1s}$ cleaves portions of both of components C4 and C2. Parts of the C4 and C2 components then combine to form the activated complex $\overline{C4ba}/$ having a molecular weight of about 280,000. $\overline{C4ba}/$ is a proteolytic enzyme which continues ongoing complement action. Earlier components are no longer required after it has been formed. $\overline{C4ba}/$ cleaves and thereby activates the next component of the sequence, C3, to produce C3b which attaches to cell membranes adjacent to the $\overline{C4ba}/$. The C3b then combines with the C4b,2a to form the last activated complex in the classical pathway $\overline{C4ba,3b}/$. This enzyme cleaves C5, a component of the membrane attack unit.

The alternative pathway, also known as the properdin pathway, comprises at least six components. Five of these components truly belong to the alternative pathway, factors B, D, properdin (P), and two inhibitors, H and I. The sixth component, C3, can also be found in the classical pathway. Component C3b is sometimes also known as factor A. The alternative pathway can be activated by immunological substances such as IgA and non-immunological substances such as certain complex polysacharides, trypsin-like enzymes and cobra venom factor. Even in the absence of any antibody or immunoglobulin, the alternative pathway can destroy microorganisms.

Activation of the alternative pathway proceeds in a different manner than activation of the classical pathway. An initial requirement is the presence of C3b which appears to be continuously generated in small amounts in the body. C3b production is thought to be due to water induced cleavage of a thioester bond in C3 forming an activated C3* which reacts with the factors B and D to generate an enzyme to cleave C3 into C3a and C3b. C3b can be further produced by a positive feedback mechanism in which factor D and Bb (a component of factor B) combine with C3b to form the activated complex C3b,Bb that acts as an enzyme in an amplification loop to cleave more C3 to form additional C3b. Factors I and H act as regulator proteins by cleaving C3b to render it inactive. Other regulator proteins include C1 inhibitor and C4 binding protein.

C3b,Bb enzyme molecules are rendered more efficient by properdin (P) which binds to the complex and stabilizes it by slowing the spontaneous dissociation of factor Bb. Both C3b,Bb and C3b,P,Bb cleave additional C3 molecules to form modified poly-C3b enzymes, $C3b_n,Bb/$ and $C3b_n,P,Bb,/$ wherein "n" is greater than 1. Any of these molecules can also cleave C5 into C5a and C5b and initate the membrane attack unit of the same common terminal trunk. The C5b then combines with C6 and C7 to form an active trimolecular complex, C5b,6,7. The C5b,6,7 then combines with C8 and a plurality of C9's to form a further, active complex, which on the surface of a cell causes cytolysis.

When either pathway of the complement system is activated, the component C3 is proteolytically cleaved into C3a and C3b. C3b, through an ester bond, can link to biological membranes or particles. C3b also cooperates with other components in the complement system such as factor B and properdin or C4b and C2a to activate the membrane attack complex of components C5 though C9.

C3b can be proteolytically cleaved by factors H and I together, or by factor I alone where the C3b is bound to a type 1 complement receptor (CR1), to generate the inactivated molecule iC3b. The iC3b molecule can then go through several degradations to form C3d, C3c and C3d,g, also known as alpha-2D. C3d,g can be cleaved to form C3d and C3g with the ester bond discussed above being on the C3d molecule. In the case of cell-bound iC3b, the degradation products C3d,g and C3d remain bound to the cell by this ester bond.

Immune complexes (ICs), composed of antigens and their respective antibodies, appear to be involved in the pathogenesis of a diverse array of human and animal diseases. These include autoimmune, infectious (bacterial, parasitic, viral), neoplastic and other unclassified disorders. The primary means by which immune complexes mediate tissue injury is activation of the complement system, resulting in release of biologically active peptides (C3a, C3dg, C5a). Along with immune complex-fixed C3 fragments, these peptides induce such biologic phenomena as immune adherence, leukocytosis, chemotaxis and release of injurious mediators and of proteolytic enzymes.

Immune complexes and C3–C5 fragments also appear to exert profound effects on a variety of immune functions, both humoral and cellular. These effects may enhance or suppress immunity depending primarily on the antigen to antibody ratio, the isotype of antibody involved, and the balance between C3 and C5 fragments. Therefore, there is a great interest in developing techniques for detection and quantitation of immune complexes and products of activated complement components. A long list of assays for immune complexes now exists, but none is specific or sensitive enough to have the diagnostic and/or prognostic value required.

U.S. Pat. No. 4,342,566 to Theofilopoulos et al. describes an assay in which solid phase-bound polyclonal anti-human C3 reacts with a test sample, and bound complement-fixing immune complexes are subsequently detected with a radiolabeled or enzyme-linked antibody to human IgG or with radiolabeled protein-A from Staphylococcus. The anti-C3 is used in its F(ab')$_2$ form to avoid false positive results caused by rheumatoid factors (anti-homologous and/or heterologous-gammaglobulin autoantibodies) that might be present. Owing to the lack of exclusive specificity for C3c or C3d of the original polyclonal anti-C3 antibody employed, the assay has not subcategorized the complement-fixing immune complexes detected according to the state of C3 that they carry (C3b, iC3b, C3d). Competition between immune complex-bound C3 fragments and nonactivated free C3 might have also reduced the assay's sensitivity.

Study and measurement of the activation of a complement pathway can provide an indication of many possible biological disorders. The two complement pathways have been implicated in the pathogenesis or symptomatology of a broad spectrum of human diseases and pathologic conditions. In the case of the classical pathway, these include immune complex diseases of several types, autoimmune diseases, in particular systemic lupus erythematosus, and infectious diseases. The alternative pathway has been found to be involved in infections with gram negative bacteria, viruses, parasites, fungi, gram negative septicemia, and various dermatologic, renal, and hematologic diseases. Alternative pathway activation has also been associated with trauma, burns and adult respiratory distress syndrome (ARDS), as well as contact with dialysis membranes such as during hemodialysis and cardiac bypass surgery. In vitro studies have indicated that a number of gram negative bacteria and bacterial products, virus infected cells, viruses, protozoa, fungi, burns, damaged and injured cells, and other substances of biomedical importance have the ability to activate the alternative pathway in human serum.

Further background information on the operation and measurement of the complement system can be found in Cooper, "The Complement System" in *Basic and Clinical Immunology*, pp. 124–135, Stites et al. editors, Lange Medical Publications, Los Altos, CA. (1982); H. Rapp and T. Borsost, *Molecular Basis of Complement Action*, pp. 81–83, Appleton Century Crafts, New York, N.Y. (1970); Muller-Eberhard, et al., *Adv. Immunol.*, 29:1–53 (1980); Pangburn et al., *J. Immunol.*, 124:977–982 (1980); Schreiber et al., *Clin. Immunol. and Immunopathol.*, 15:384–396 (1980); Platts-Mills et al., *J. Immunol.*, 113:348–357 (1974); Lesavre et al., *J. Immunol.*, 123:529–534 (1979); Polhill et al., *J. Immunol.*, 121:363–370 (1978); Fearon et al., *J. Immunol.*, 115:1357–1361 (1975); Day et al., *Scand. J. Immunol.*, 5:715–720 (1976); Chapitis et al., *J. Exp. Med.*, 143:241–257 (1976).

SUMMARY OF THE INVENTION

The present invention teaches a method and assay system useful for determining the character of various complement component fragments in a sample such as serum. It is possible to detect the presence and measure the amount of various C3 fragments in a sample. The C3 fragments can either be fluid phase within the sample or cell-bound as with complement fixing immune complexes.

In one aspect of the invention, a plurality of specific binding agents to various C3 fragments bound to an immune complex are reacted with a sample of serum. The amount of binding by each specific binding agent is then measured and the values obtained are used to calculate the amount of particular C3 fragments in the sample. The sample can be reacted with each agent or preferably, the sample is divided into parts with each part being reacted with a different agent.

As an illustration, the amount of C3d,g which bearing immune complexes can be determined by reacting a first specific binding agent for C3d with at least portion of the sample and measuring the amount of binding of the first specific binding agent with any C3d present. A second binding agent specific for C3c is also reacted with at least a portion of the sample and the amount of binding by this agent is also measured. The first binding agent specific to C3d reacts with C3b, iC3b, and C3d,g. The second binding agent specific to C3c reacts with C3b and iC3b. By subtracting the measured value obtained using the C3c binding agent from the measured value obtained using the C3d specific binding agent, one is able to determine the amount of C3d,g bearing immune complex to present in the sample.

Other advantages and features of the present invention will become readily apparent to those skilled in the art from the following description of the invention, the drawings and the appended claims.

BRIEF DESCRIPTION OF THE DRAWINGS

In the drawings forming a part of the disclosure of this invention.

The graphs of FIGS. 2 through 7 illustrate results of solid phase radioimmune assays of the specificities of various monoclonal (Mc) or polyclonal (Pc) antibodies for either C3b or C3c. In each assay, a microtiter plate well was coated with the indicated antibody in an amount shown on the abscissa. $^{125}$I-labeled C3b or C3c was then added to the plates. The amount of each component that bound to the plate is shown on the ordinate.

Figure 8:
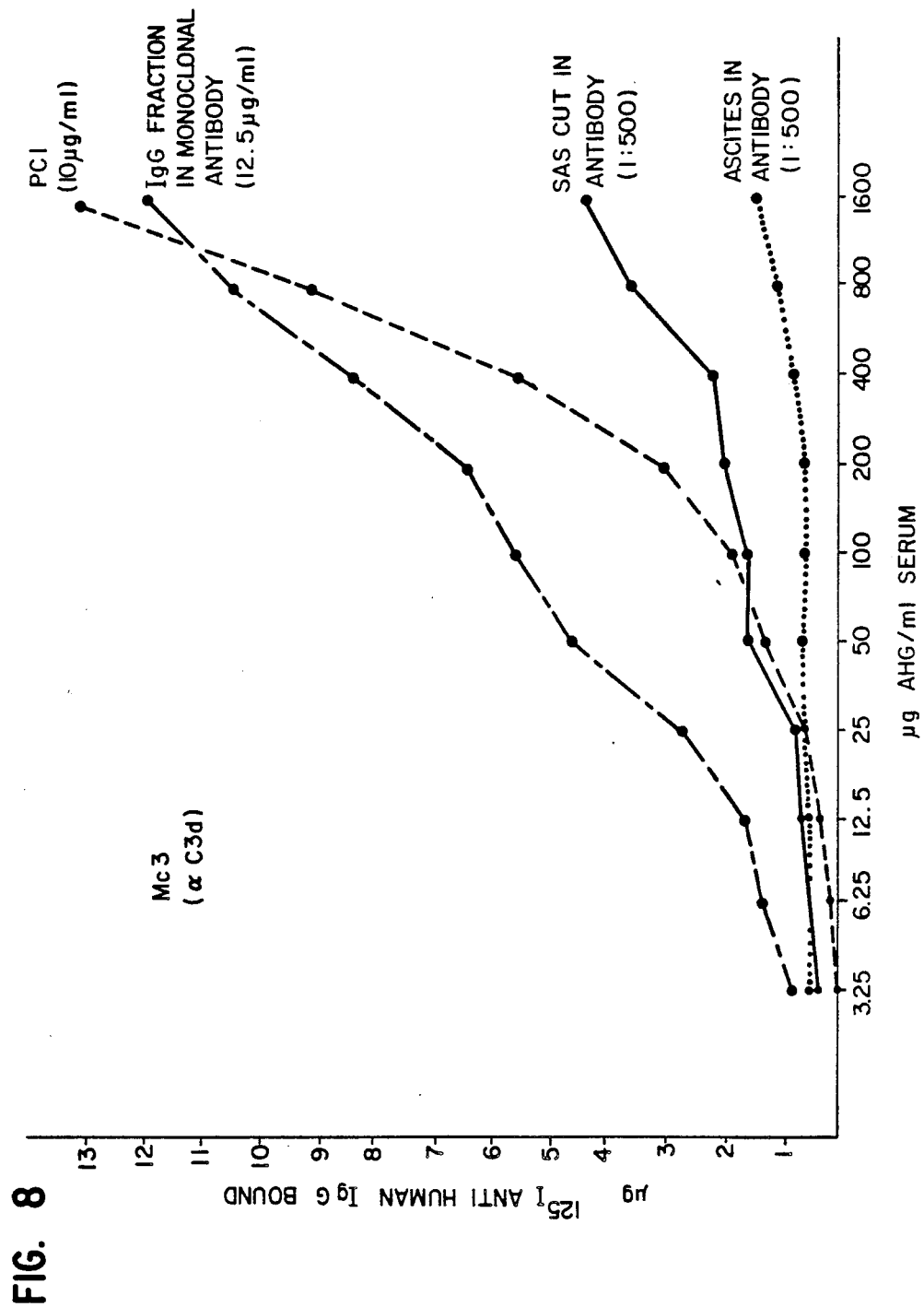
Figure 9:
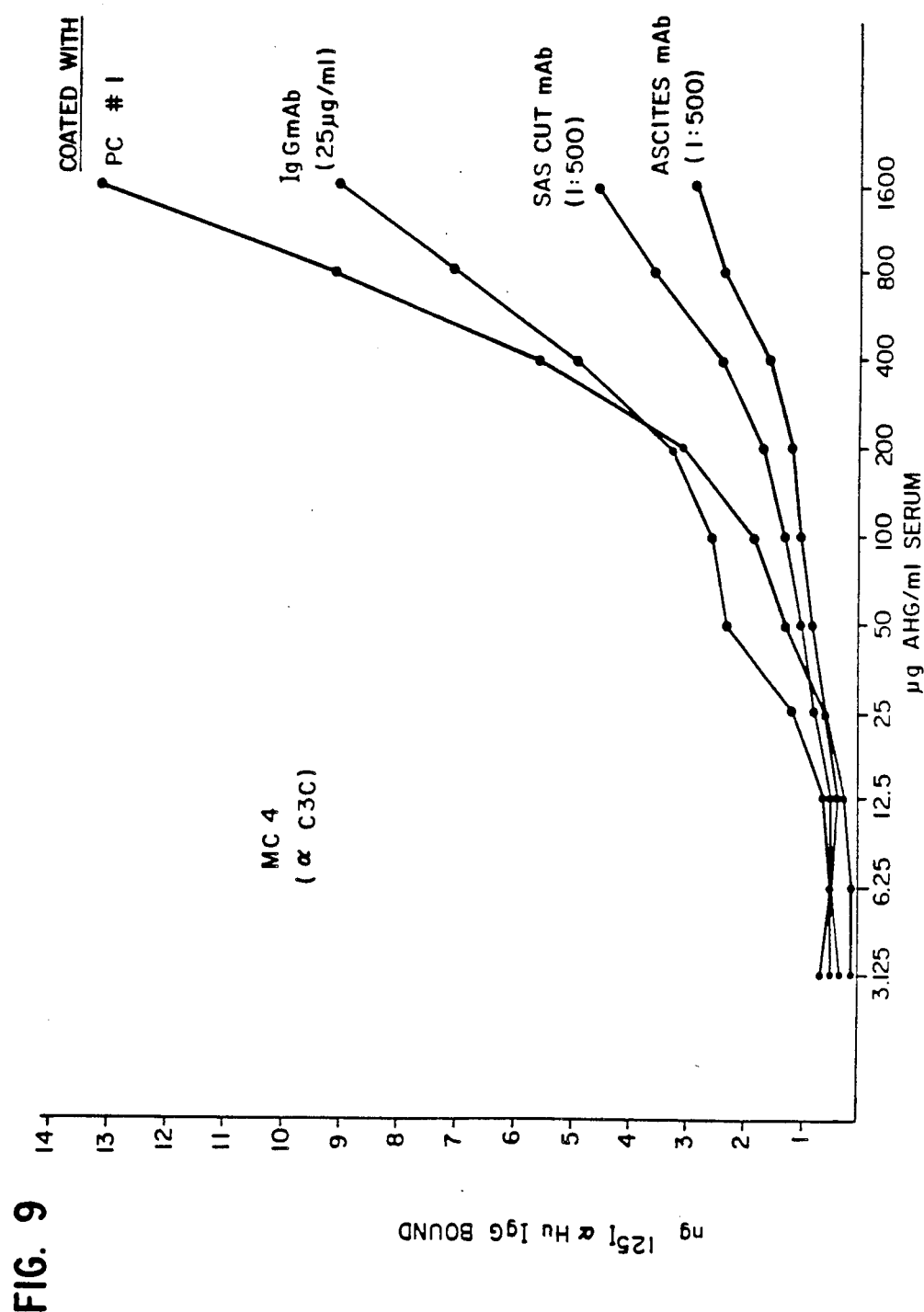
Figure 10:
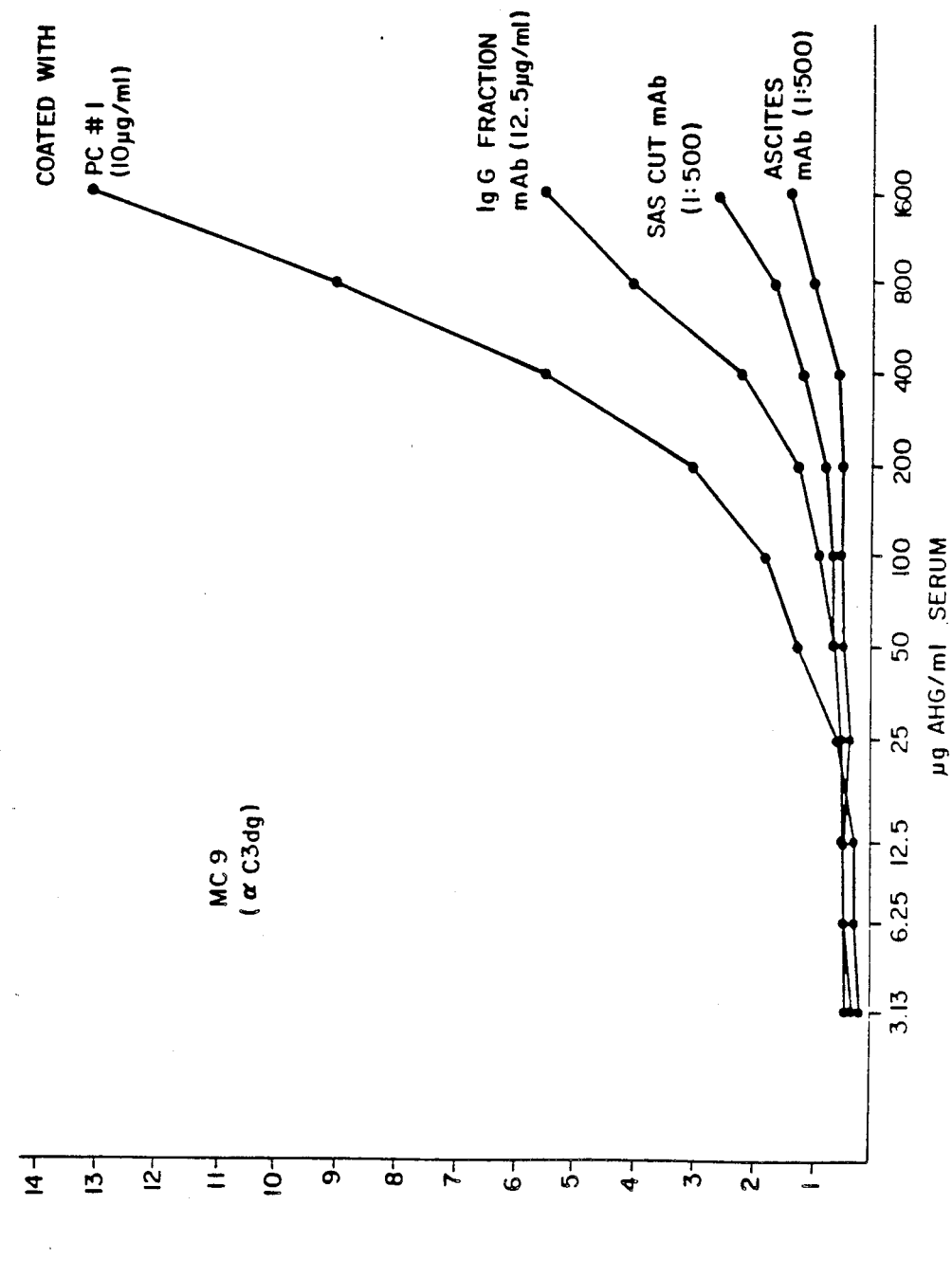
Figure 11:
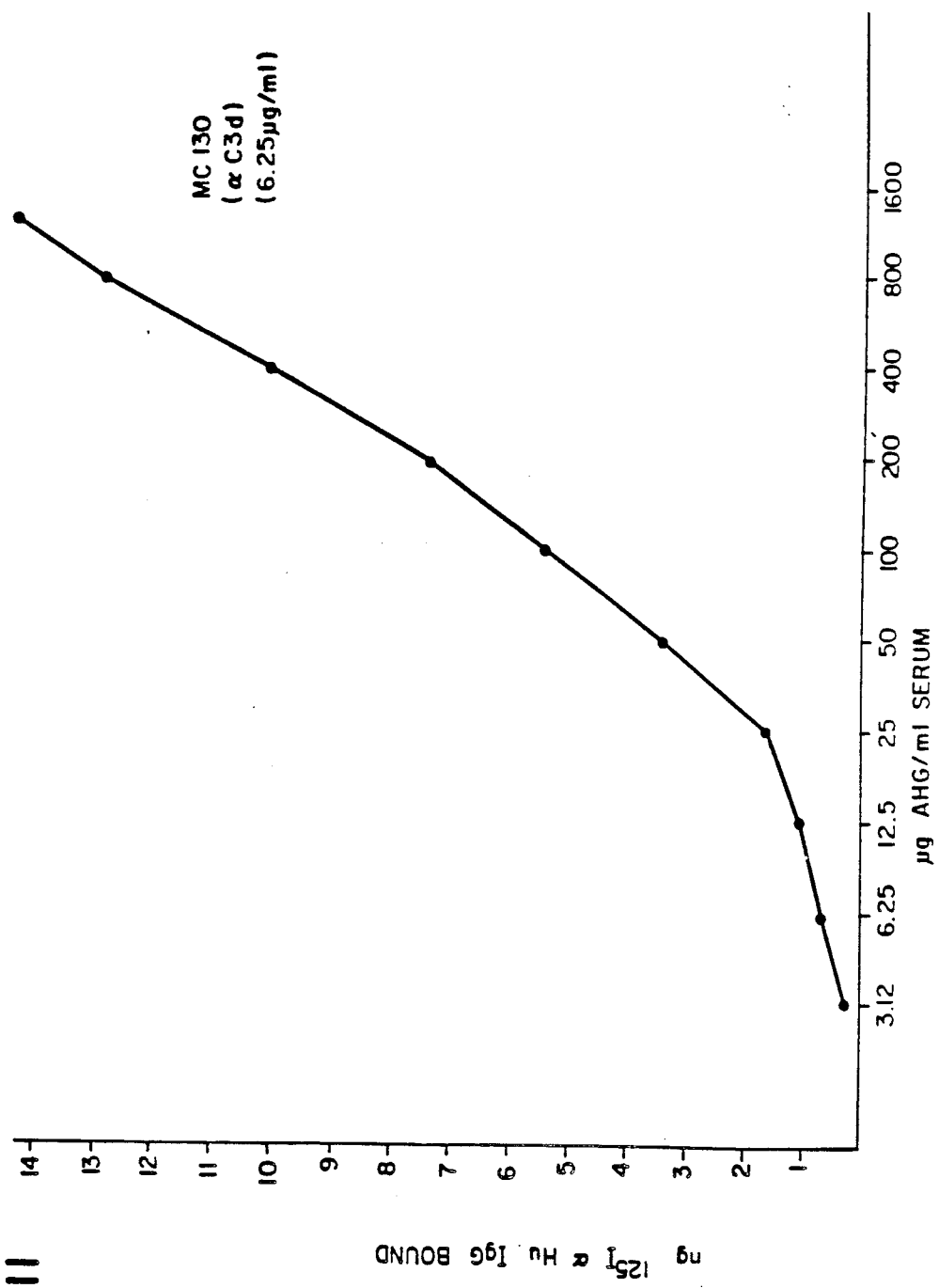
Figure 12:
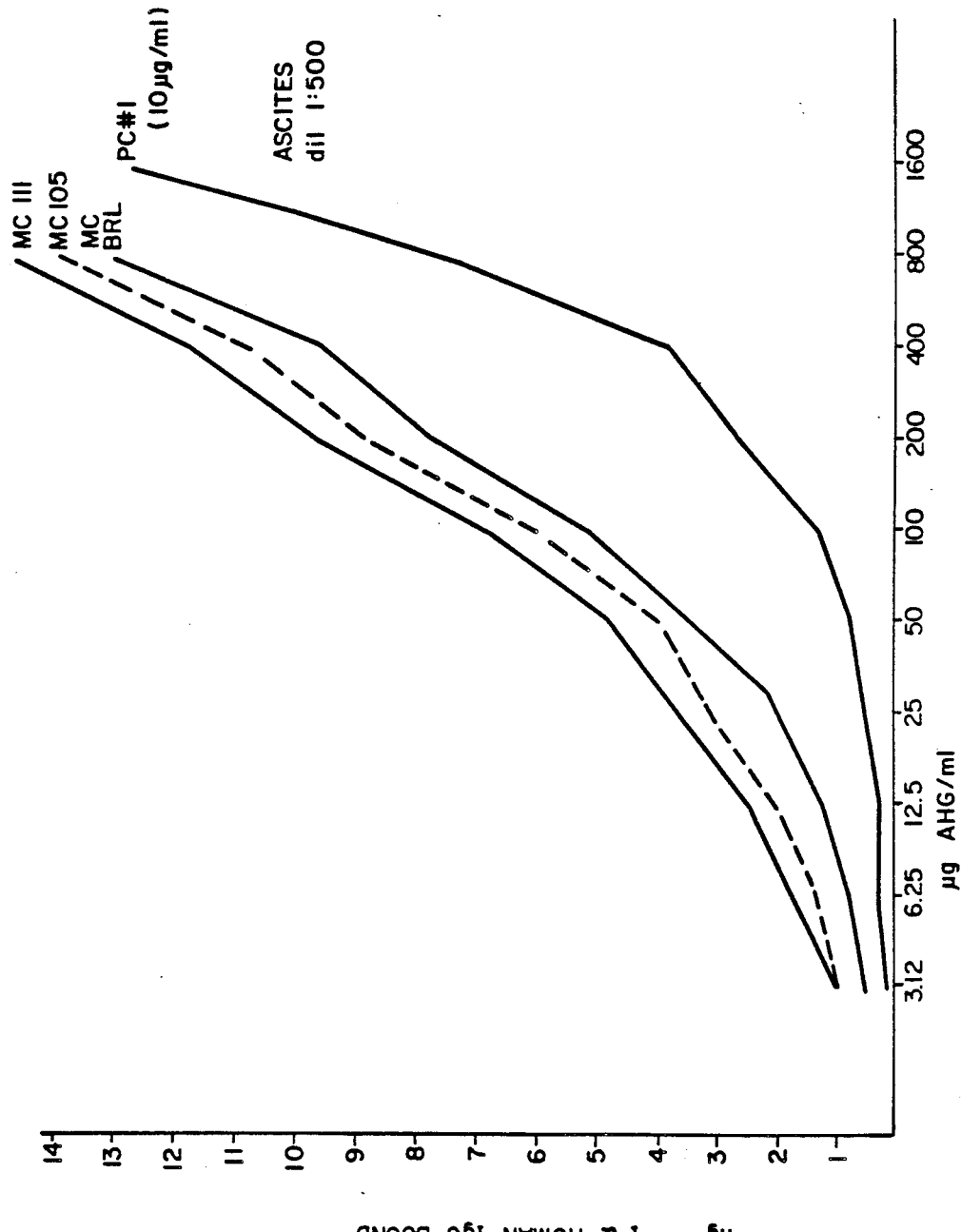
Figure 13:
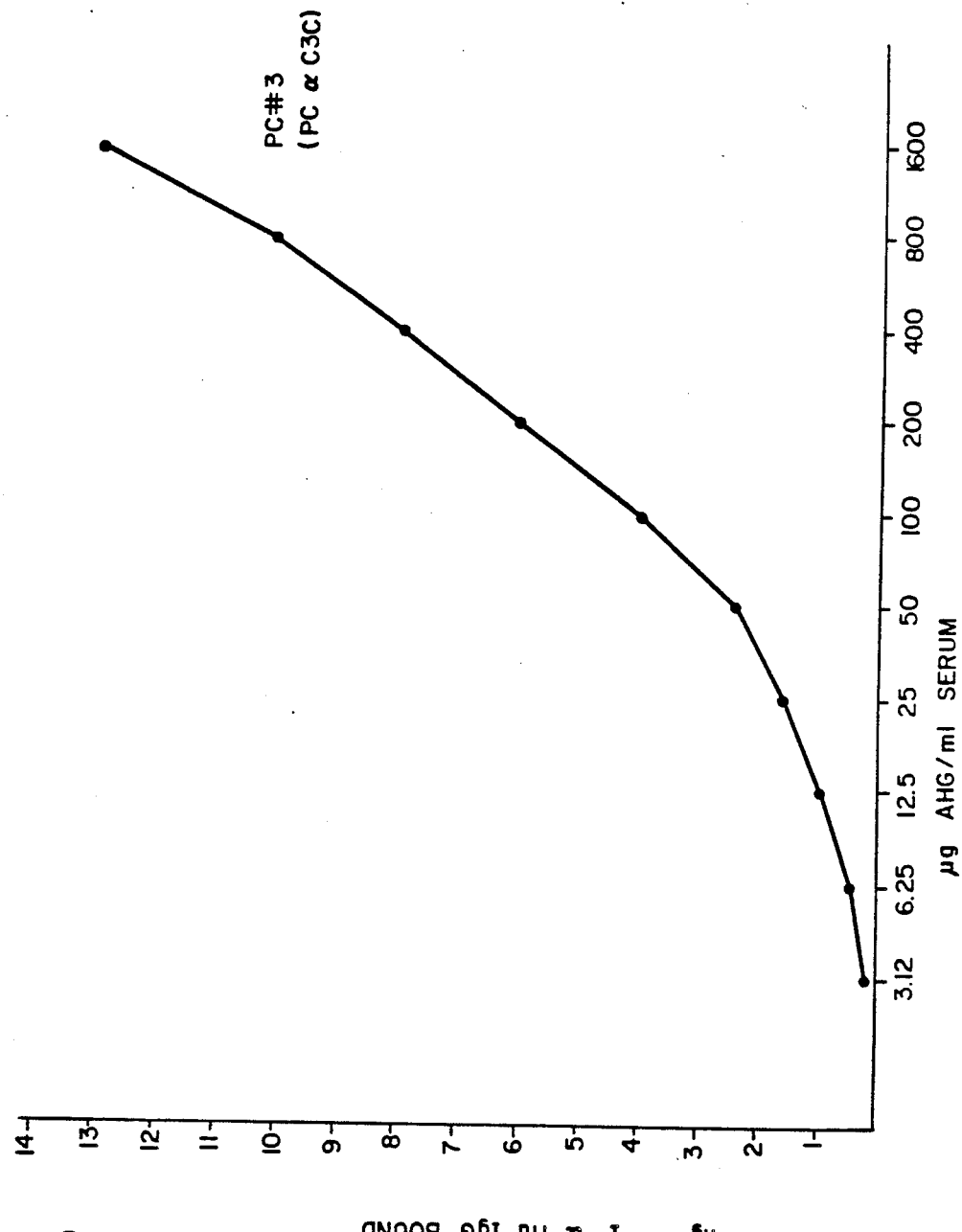
Figure 14:
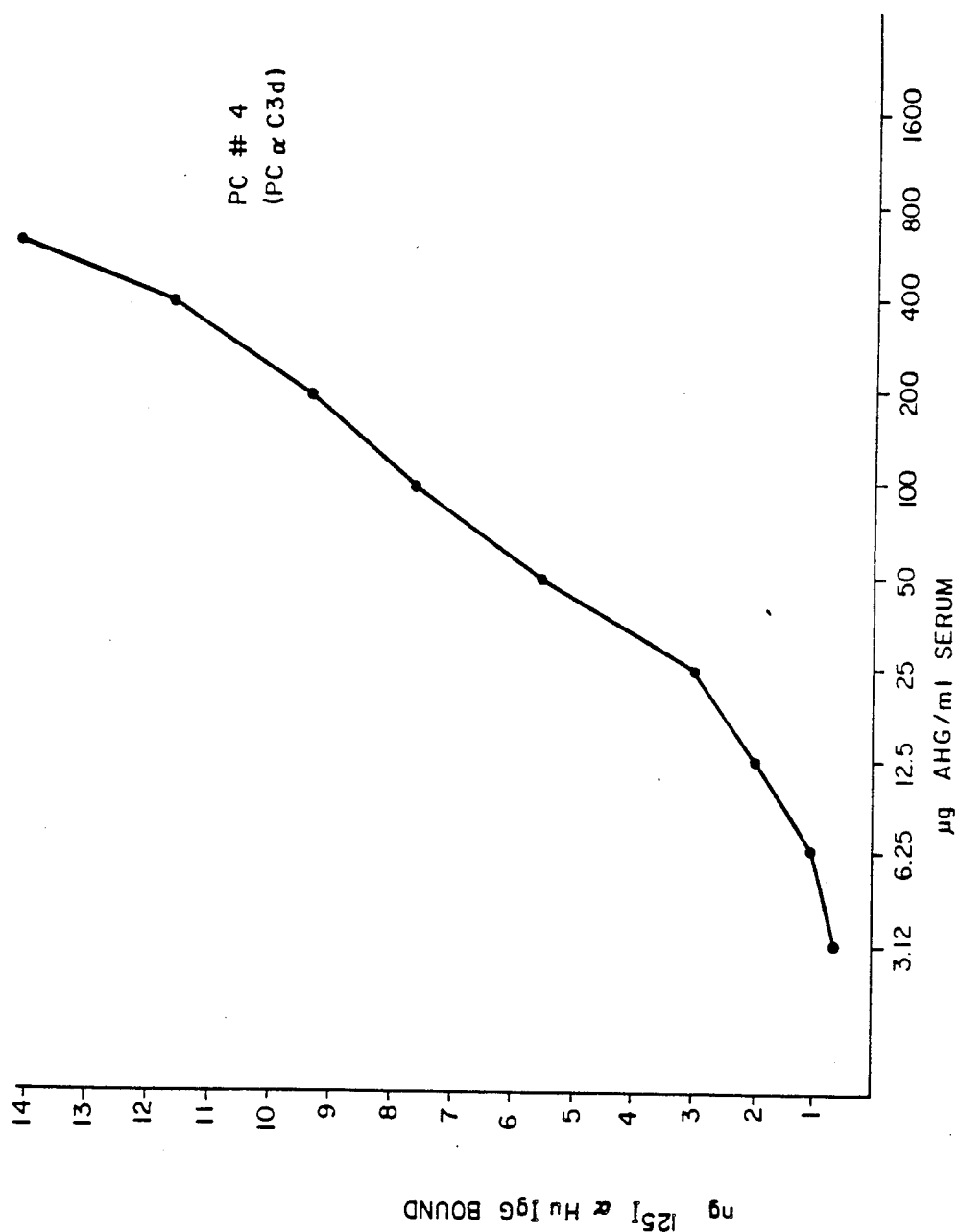
Figure 15:
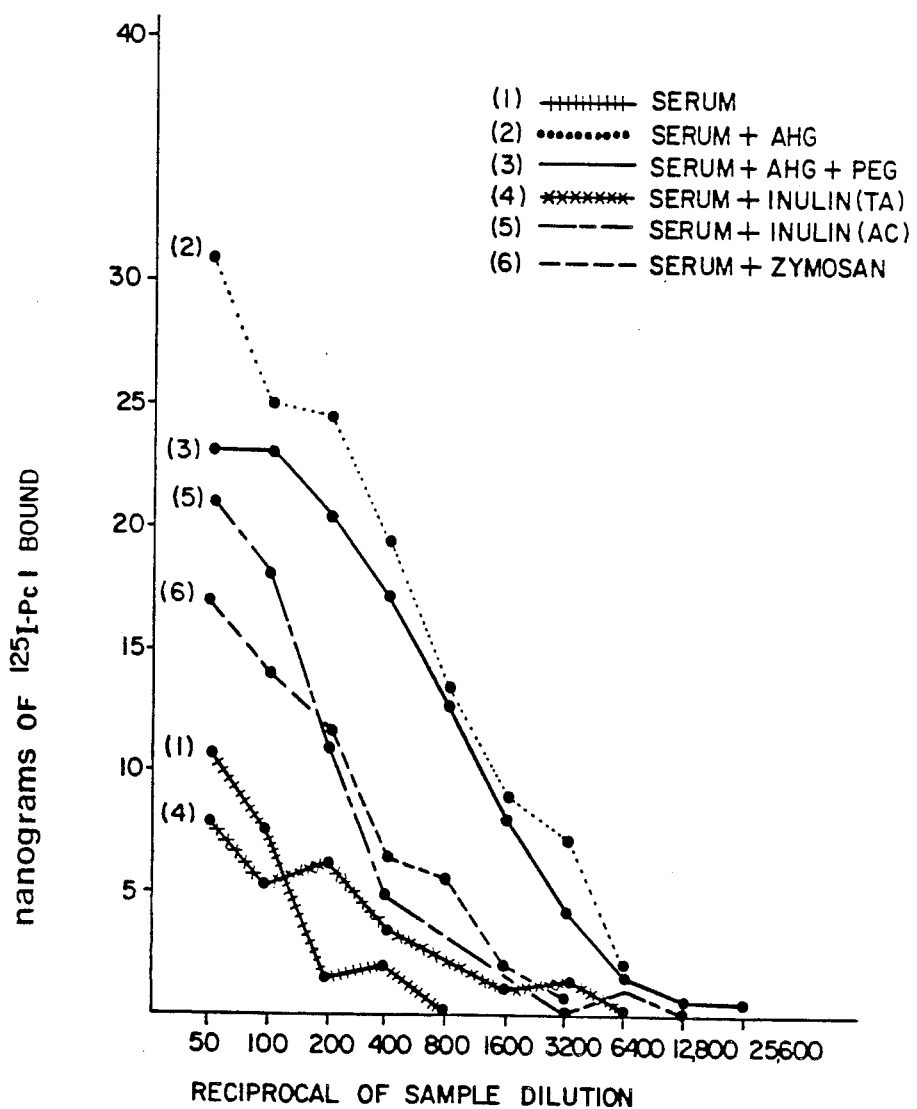
Figure 16:
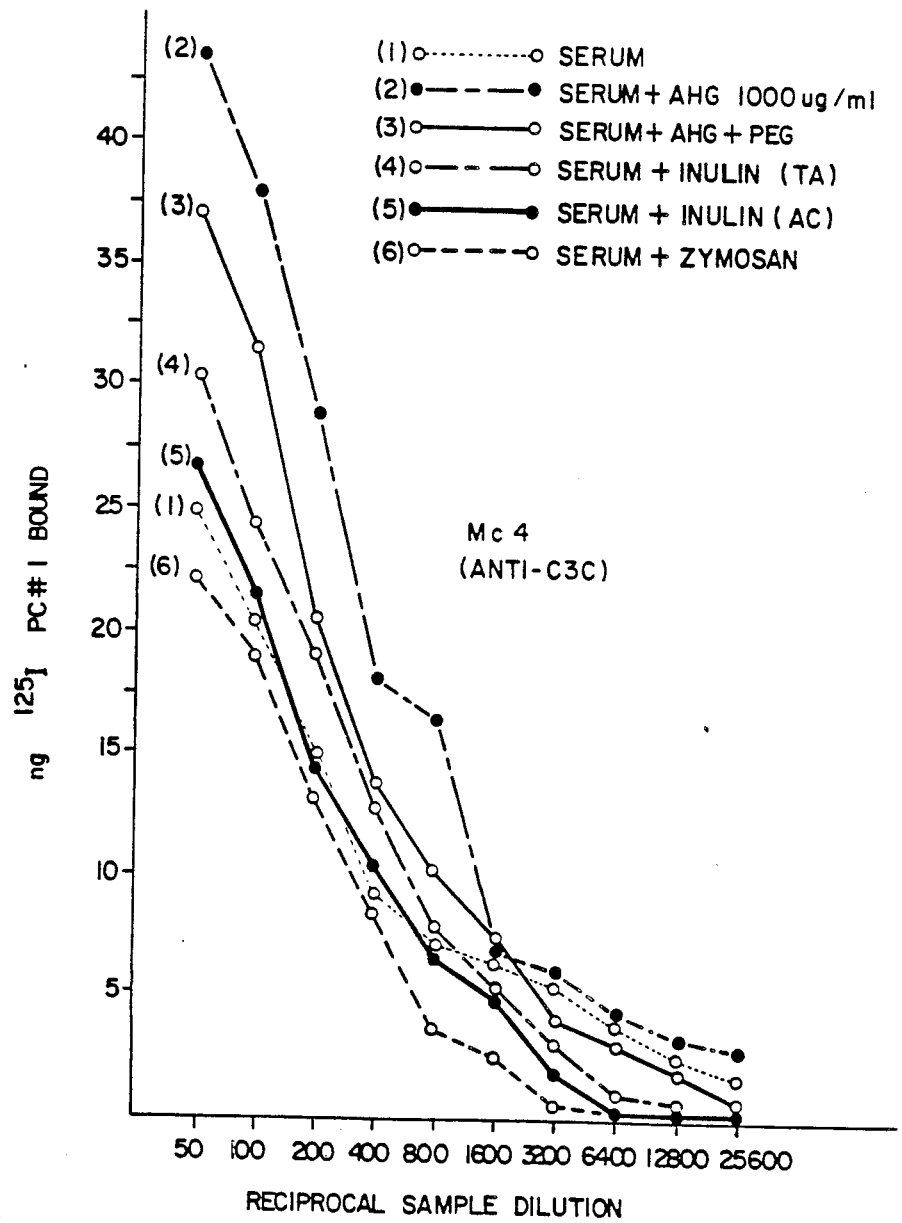
Figure 17:
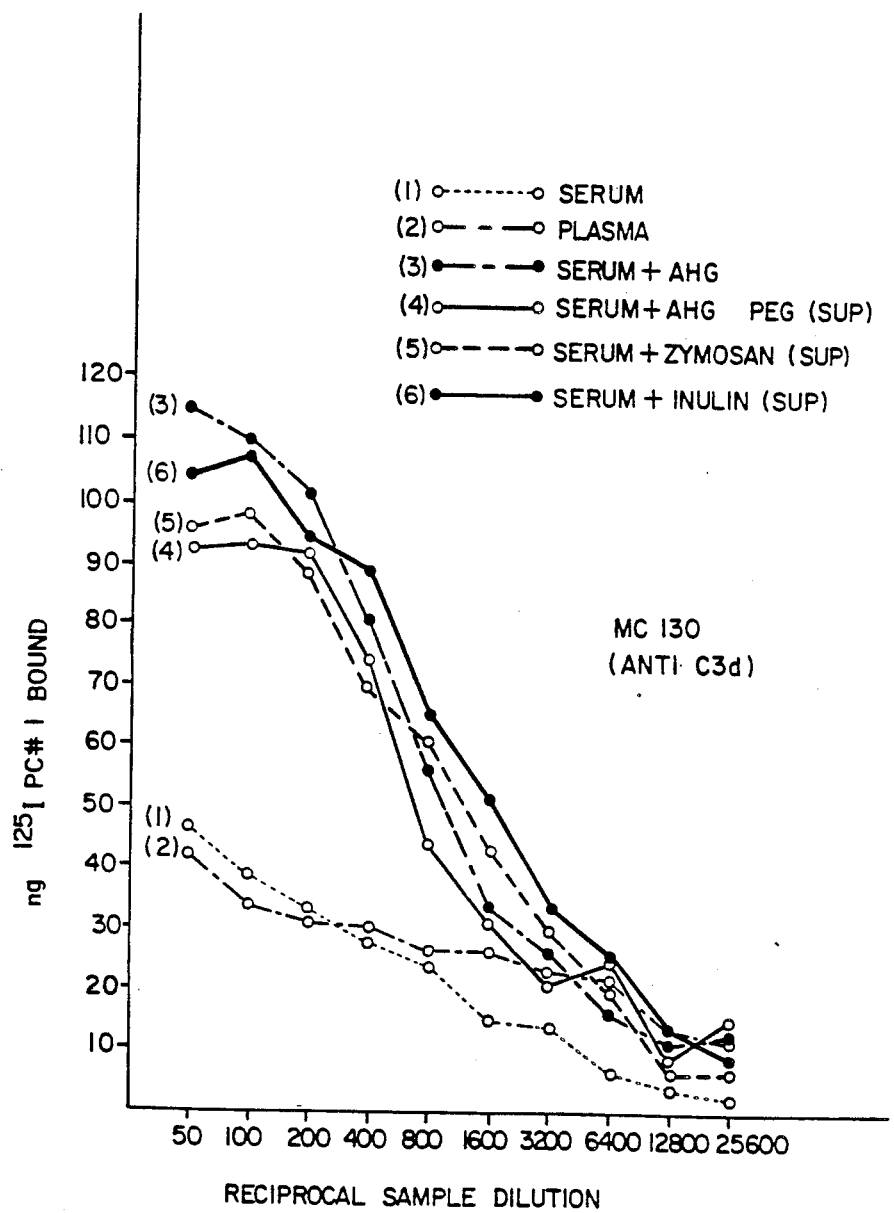
Figure 18:
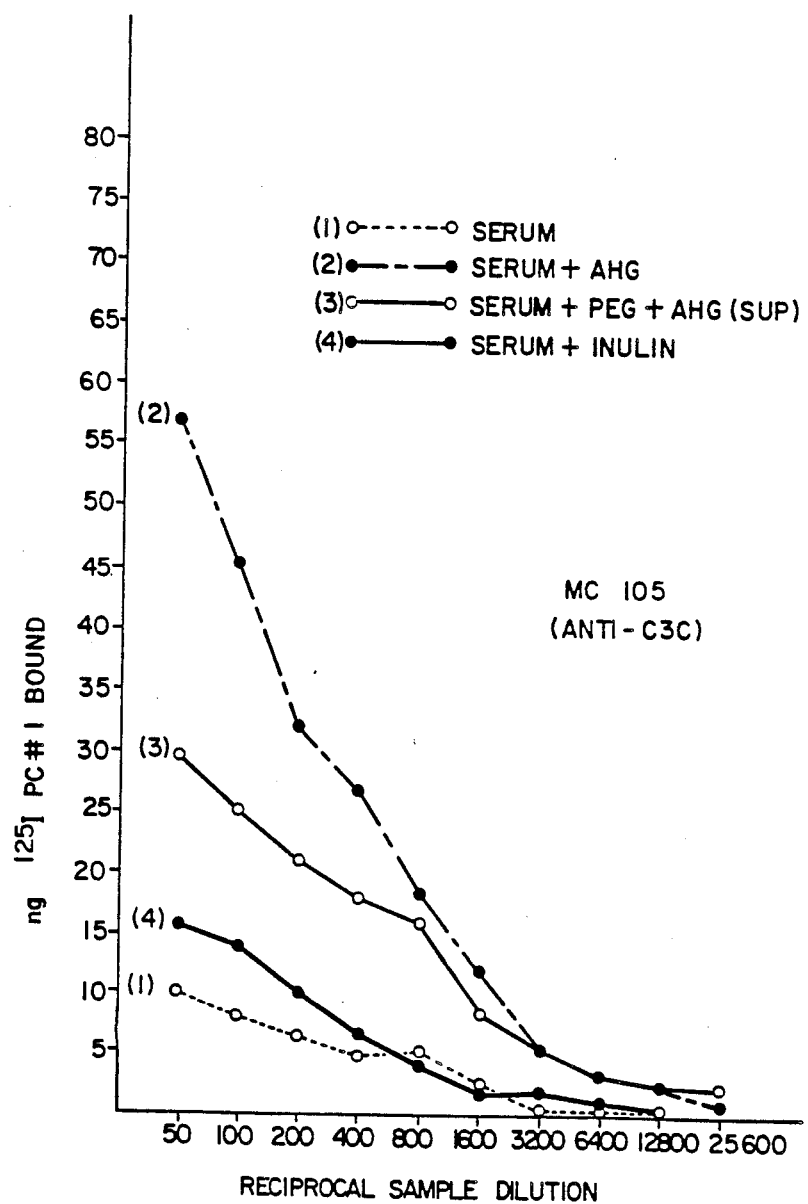
Figure 19:
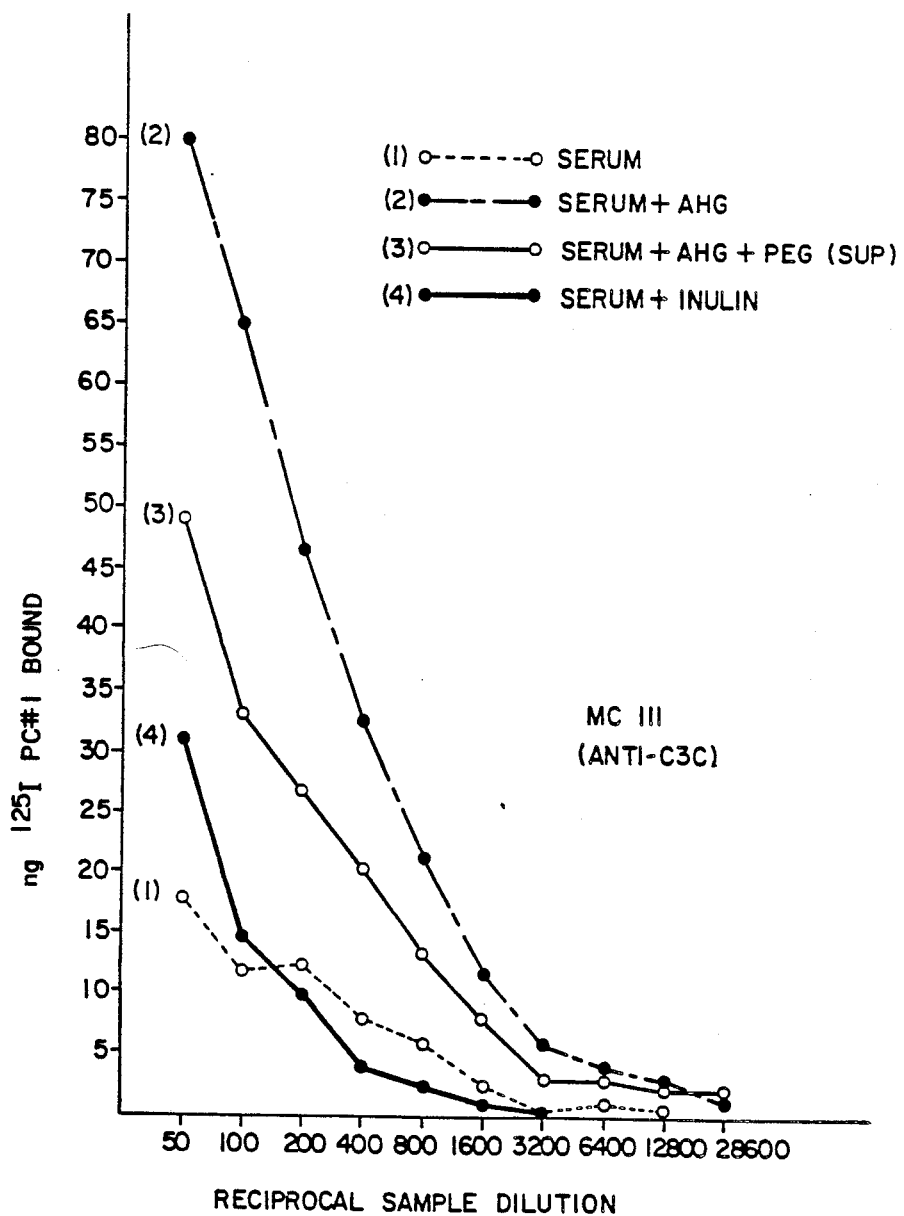
Figure 20:
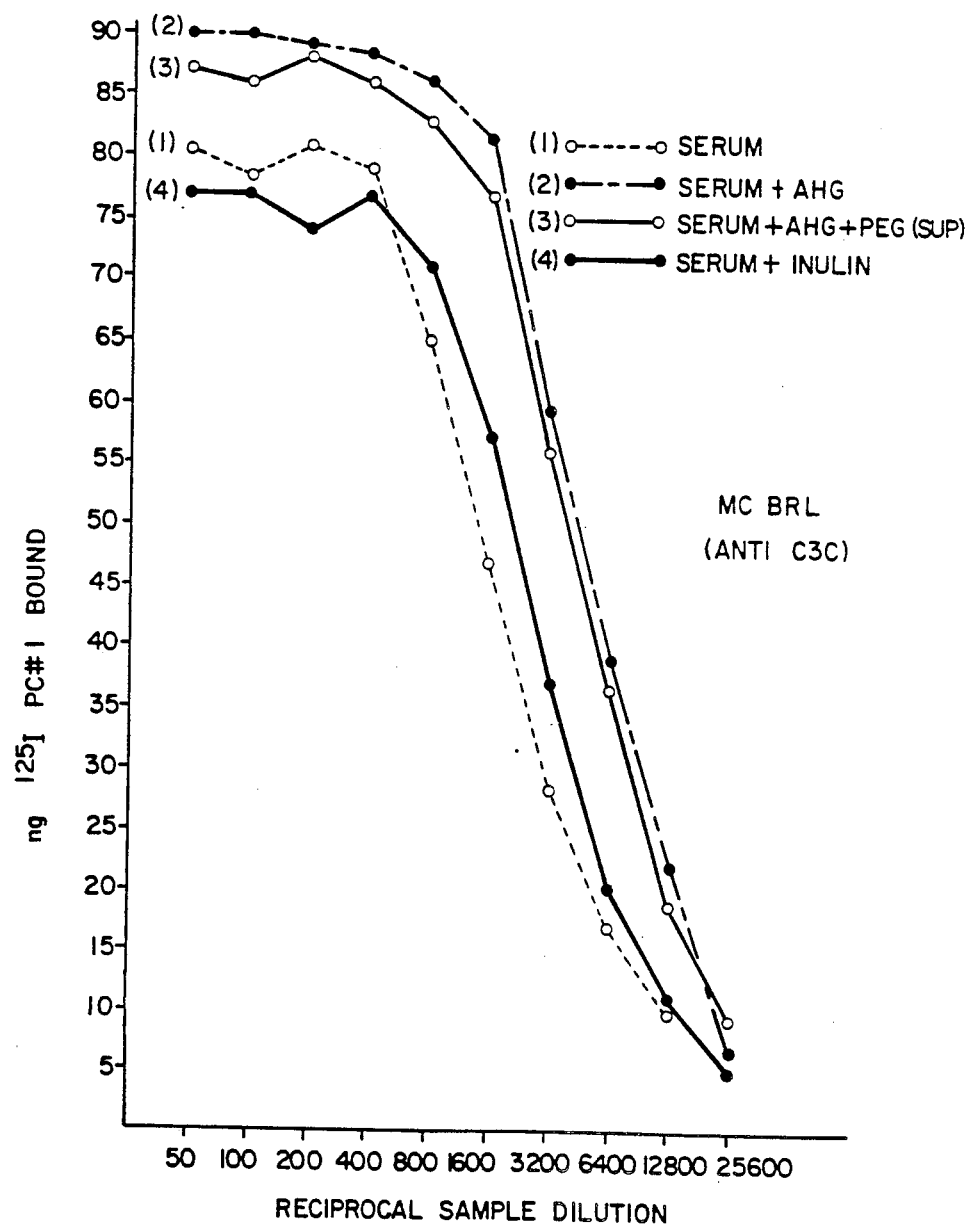
Figure 21:
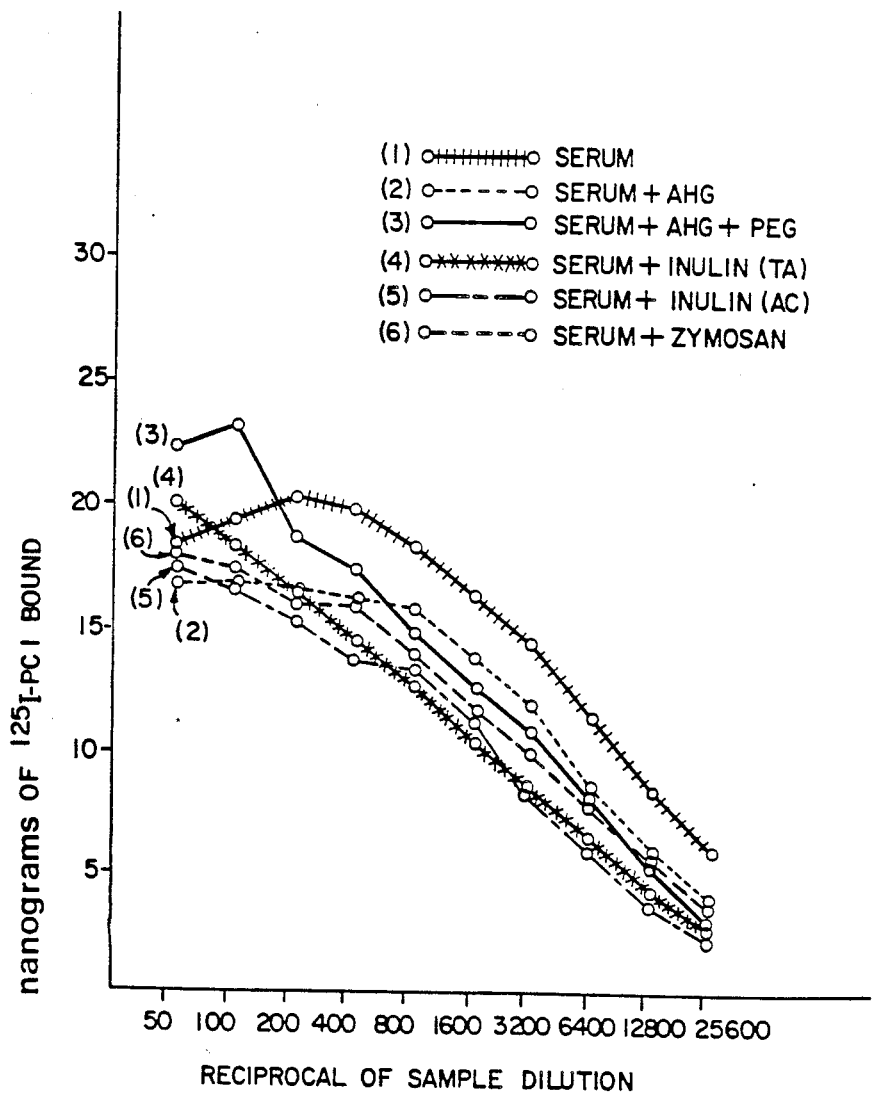
Figure 22:
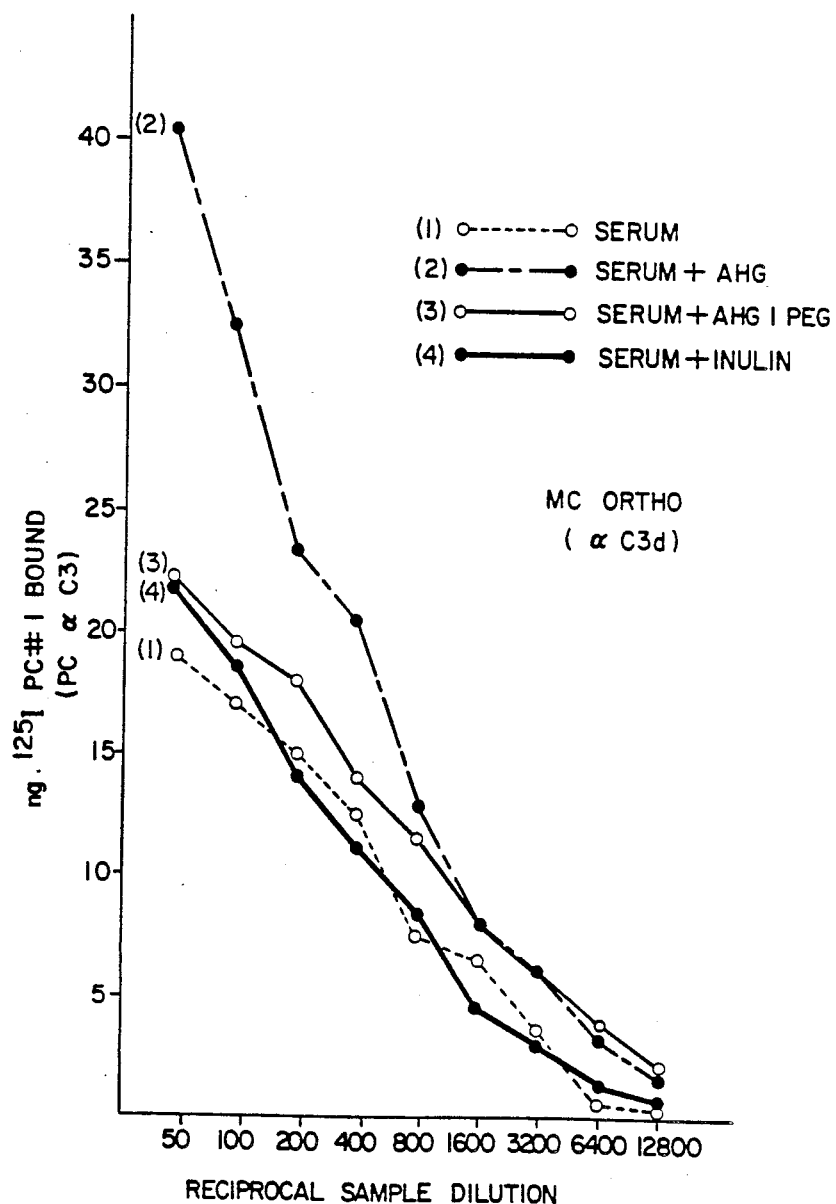

The graphs of FIGS. 8 through 14 illustrate the in vitro detection of aggregated gamma globulin in human serum as a model immune complex by each of the monoclonal (Mc) or polyclonal (Pc) antibodies noted. In each assay, the antibody as a whole preparation, as ascites fluid or as a saturated ammonium sulfate cut of ascites fluid was coated on the wells of microtiter plates in the amounts shown. The plates were rinsed and aggregated human gamma globulin (AHG) in the amounts shown on the abscissas was add to each well. The wells were incubated and rinsed again. Thereafter, $^{125}$I-labeled anti-human IgG was added to the wells and the amount of those antibodies that bound was determined as is shown on the ordinates. Saturated ammonium sulfate (SAS) cuts of ascites fluid were prepared as discussed in Weir, *Handbook of Experimental Immunology*, Blackwell Scientific Publications, London 2nd ed., (1973). FIGS. 8, 9 and 10 also illustrate control results using the polyclonal antibody PC1 or PC1 #1.

The graphs of FIGS. 15 through 22 illustrate the reactivities of the monoclonal (Mc) or polyclonal (Pc) antibodies with native C3 and with activated C3 fragments free in solution or bound to aggregated human gamma globulin (AHG) as immune complex models. Here, the microtiter plate wells were coated with the appropriate antibodies in the amounts shown in the abscissas, the enumerated materials such as serum, serum plus AHG and the like as shown were then added to separate wells and the admixtures incubated. The incubated admixtures were then rinsed and 1000 nanograms, of $^{125}$I-labeled, polyclonal antibody Pcl ($^{125}$I-Pcl or $^{125}$I PC #1) were added. The amount of antibody Pcl that bound to the plates was measured. Where two phase compositions of added, enumerated, materials were prepared, such as with mixtures of serum plus aggregated human gamma globulin (AHG) plus polyethyleneglycol (PEG), or serum plus zymosan or inulin, the supernates (sup) of those mixtures were added to the microtiter plate wells.

DESCRIPTION OF THE PREFERRED EMBODIMENTS

I. Assay to Determine the Character and Amount of Complement Component Fragments.

The present invention is directed to a method and assay system for determining the character of various complement component fragments in a sample of body fluid such as such as serum. One can detect the presence and measure the amount of various C3 fragments in the sample. The C3 fragments can either be fluid phase within the sample or immune complex-bound by a complement fixing immune complex.

To date, there are certain C3 fragments which do not have a specific antibody to that fragment alone. As an example, an antibody to C3d will also bind with C3b, iC3b, and C3dg since all of these fragments include the C3d moiety.

In one embodiment of the invention, a plurality of specific binding agents to various C3 fragments are reacted with a serum sample. The amount of binding by each specific binding agent is then measured and the values obtained used to calculate the amount of particular C3 fragments in the sample. The calculations can be done according to the equations shown in Table III.

As an illustration, the amount of C3d,g bearing immune complexes can be determined by binding a first specific agent to C3d present in the sample and measuring the amount of binding. A second binding agent specific for C3c is also reacted with the sample and the amount of binding measured. The C3d specific binding agent reacts with C3b, iC3b, and C3d,g bearing immune complexes, while the C3c specific binding agent reacts with C3b and iC3b bearing immune complexes. Thus, by subtracting the value obtained from the C3c binding agent from the value obtained using the C3d specific binding agent, one is able to determine the amount of C3d,g bounmd to immune complexes present in the sample. Other C3 fragments can also be investigated as well as various C1 fragments.

The sample can be analyzed by the various specific binding agents at the same time. However, it is preferred to divide the sample into parts with each part being subjected to different specific binding agents. The parts are preferably of the same volume so comparison of the values is simplified, but where different volumes are used, appropriate mathmetical corrections can easily be made.

The method described can be practiced with an assay system of the present invention. The assay system includes, in kit form, a first specific binding agent for a first C3 fragment together with first means for measuring the amount of first specific binding agent bound to the first C3 fragment. A second specific binding agent specific to a second C3 fragment is also provided as are second means for measuring the amount of second specific binding agent bound to the second C3 fragment. By comparing the values obtained by the first measuring means with the values obtained by the second measuring means, it is possible to calculate the amount of a particular C3 fragment present in the sample.

The various means for measuring include radioimmunoassay (RIA) and enzyme-linked immunoassay (ELISA). These various measuring means are well known in the art and are discussed in Maggio *Enzyme-Immunoassay* published by CRC Press (1980), incorporated by reference.

In still another embodiment of the present invention, the particular type of C3 fragment that is bound to an immune complex is determined. This is done by reacting the specific binding agent for a particular complement component fragment such as C3d within the sample and measuring the amount of binding agent which binds to the immune complex. This method is best done in a diagnostic system which includes a binding agent specific to either the complement component fragment or a component of the immune complex. A second specific binding agent is also provided which is specific to the other of the complement component fragment or the component of the immune complex. For ease of illustration, it will be assumed that the first specific binding agent binds to the complement component fragment C3d and the second specific binding agent binds to the Fc portion of an antibody forming part of the immune complex.

The second specific binding agent also includes a label such as a radioactive isotope or an enzyme. After the two specific binding agents have reacted with the complement fixing immune complex to form an aggregate, any second specific binding agent that is not part of the aggregate is removed. The amount of remaining labeled second specific binding agent can then be measured.

The separation of unbound second specific binding agent from the aggregate can be done most easily by immobilizing the first specific binding agent on a solid matrix such as a microtiter plate. Thus as described, the first specific binding agent to C3d is immobilized on the microtiter plate and the second binding agent to the Fc portion of the antibody in the immune complexes is then reacted with the bound complex.

In a further embodiment of this concept, specific types of antibodies are used to determine the type of antibody forming the immune complex. Thus, an anti-IgG or anti-IgM can be used to determine the class of the antibody forming the immune complex. In addition, antibodies to the various subclasses can also be used.

It has been found that patients suffering from autoimmune diseases such as SLE and rheumatoid arthritis have a higher amount of cell-bound C3d in their sera than cell-bound C3c. For various parasitic diseases it has been found that these amounts are roughly equivalent. The diagnostic value of such a measurement is thus readily apparent.

In a still further embodiment of the invention, measurements can be made between the differences in the amount of complex-bound C3 fragments and fluid phase C3 fragments. Immune complex-bound C3 fragments can be removed before analysis by polyethylene glycol precipitation. Thus, a specific binding agent to a certain C3 fragment can be reacted with a serum sample and used to measure the sum of complex-bound C3 fragments and fluid. Phase C3 fragments. A similar sample of serum is then treated with polyethylene glycol to remove the complex-bound C3 fragments and the treated sample is then used to detect the amount of fluid-phase C3 fragments. By simple subtraction, this provides an indication of the amount of complex-bound C3 fragments in the original sample.

The study of the amount of various C3 fragments on immune complexes can be used to study the proteins involved in degrading C3b to C3d or as an indirect measurement of the activity of cell receptors such as the CR1 receptors on human erythrocytes.

The specific binding agents are preferably antibodies, but can also be portions of the antibodies which include the idiotype of the antibody such as the F(ab)2 portion. Other specific binding agents can also be used such as Bovine conglutin in which is specific to cell bound iC3b. The term "receptor" as used in this application is meant to indicate an antibody or the idiotype-containing polyamide portion of an antibody. Antibodies or the idiotype-containing polyamide portions of antibodies are biochemically active in that they bind at least with an antigenic ligand when admixed therewith in aqueous solution, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polyamide portions of antibodies are the portions of antibodies that bind to an antigen ligand. Such portions include the Fab, Fab', and F(ab')2 fragments prepared from antibodies by well-known enzymatic cleavage techniques.

The receptor molecules can be polyclonal as is the case for the antibodies raised to a whole protein molecule. The receptors can also be oligoclonal such as those that are raised to a polypeptide immunogen as is discussed in Sutcliffe et al., *Science*, 219, 660–666 (1983), and in the articles cited therein.

The receptors can also be monoclonal. Techniques for preparing monoclonal antibodies are well known. Monoclonal receptors useful in this invention can be prepared using a whole protein immunogen, as is customary, or by using a polypeptide as immunogen as described in Niman et al., *Proc. Natl. Acad. Sci. USA*, 80, 4949–4953 (1983). Monoclonal antibodies are typically obtained from hybridoma tissue cultures or from ascites fluid obtained from animals into which the hybridoma tissue was introduced.

Antibodies to the various C3 fragments can either be derived from monoclonal sources or polyclonal sources by use of purified C3 fragments. The preparation and forming of the antibodies is well known in the art and need not to be described in detail. See Kennett et al., *Monoclonal Antibodies, Hybrodomas: A New Dimension To Biological Analysis And Marchalonis et al. Antibodies' Tool, The Applications Of Immunochemistry*, incorporated by reference. Instead of polyclonal antibodies, monoclonal antibodies can also be used.

Recently monoclonal anti-C3 antibodies were described by Lachmann, et al. Immunol. 41:503–515 (1980); Burger, et. al. J. Immunol. 129:2041–2050 (1982); Tamerius, et al. J. Immuno. 128.512–514 (1982); and Geides, et al. Immunol. 45:645–653 (1982). Some of these monoclonals recognize neoantigenic determinants expressed on activated but not native C3, whereas others recognize C3c but not C3d, and vice versa. Use of these monoclonal antibodies can increase the sensitivity of an anti-C3 assay and can, in addition to fragment specific polyclonal anti-C3c or anti-C3d antibodies, allow subcategorization of complement-fixing immune complexes according to the C3 fragments that they carry.

Figure 1:
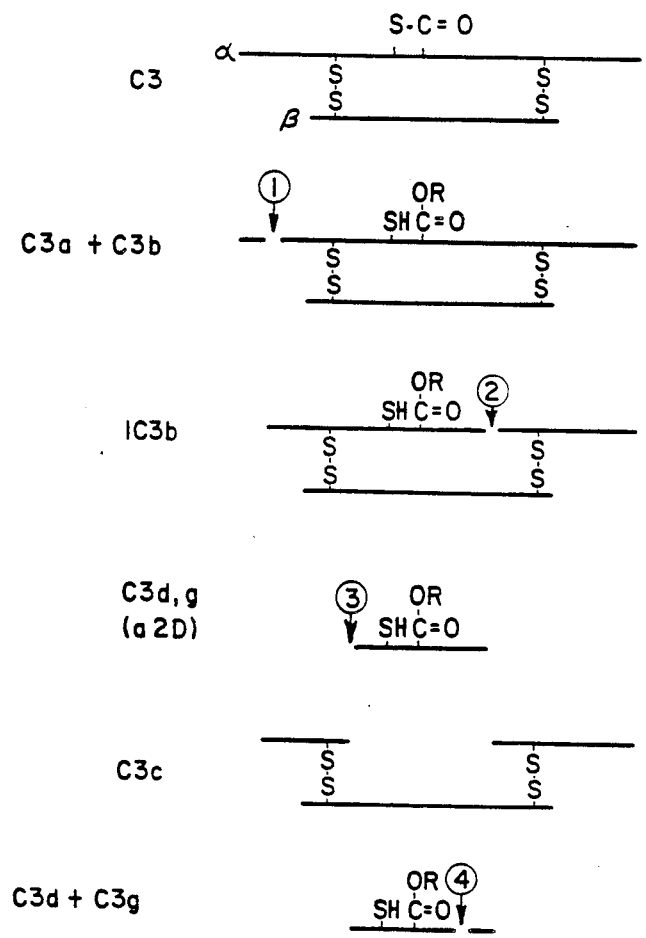
FIG. 1 illustrates a schematic representation of complement component C3 and its various cleavage products wherein circled numerals (1, 2, 3 and 4) adjacent vertical arrows indicate approximate positions of cleavage of component C3 or its degradation products to form the subsequently produced degradation products. The drawing is copied from Fearon and Wong, Ann. Rev. Immunol., Paul, Fathman and Metzger, eds., Ann. Rev. Inc. Palo Alto, CA, 1983.
Figure 2:
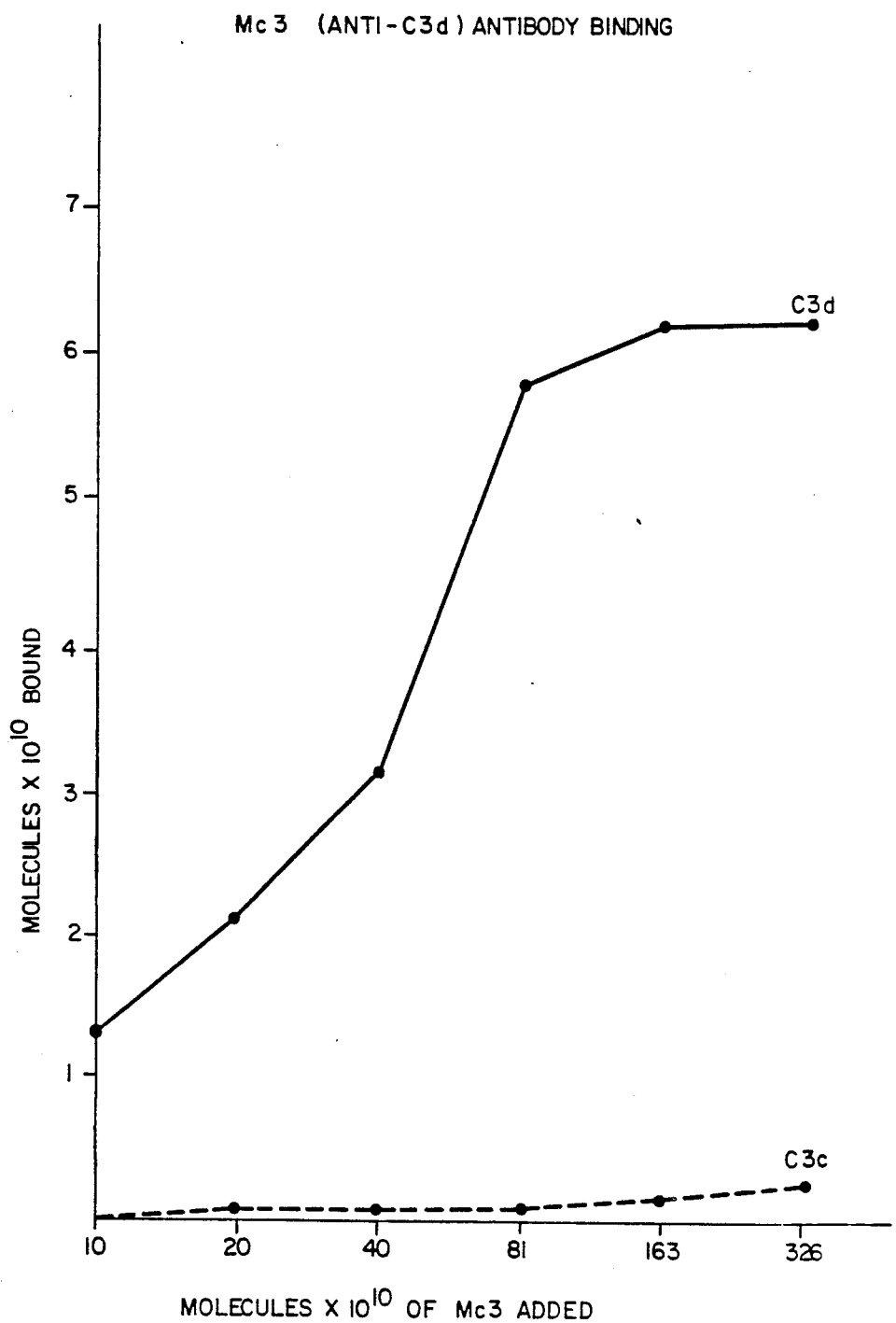
Figure 3:
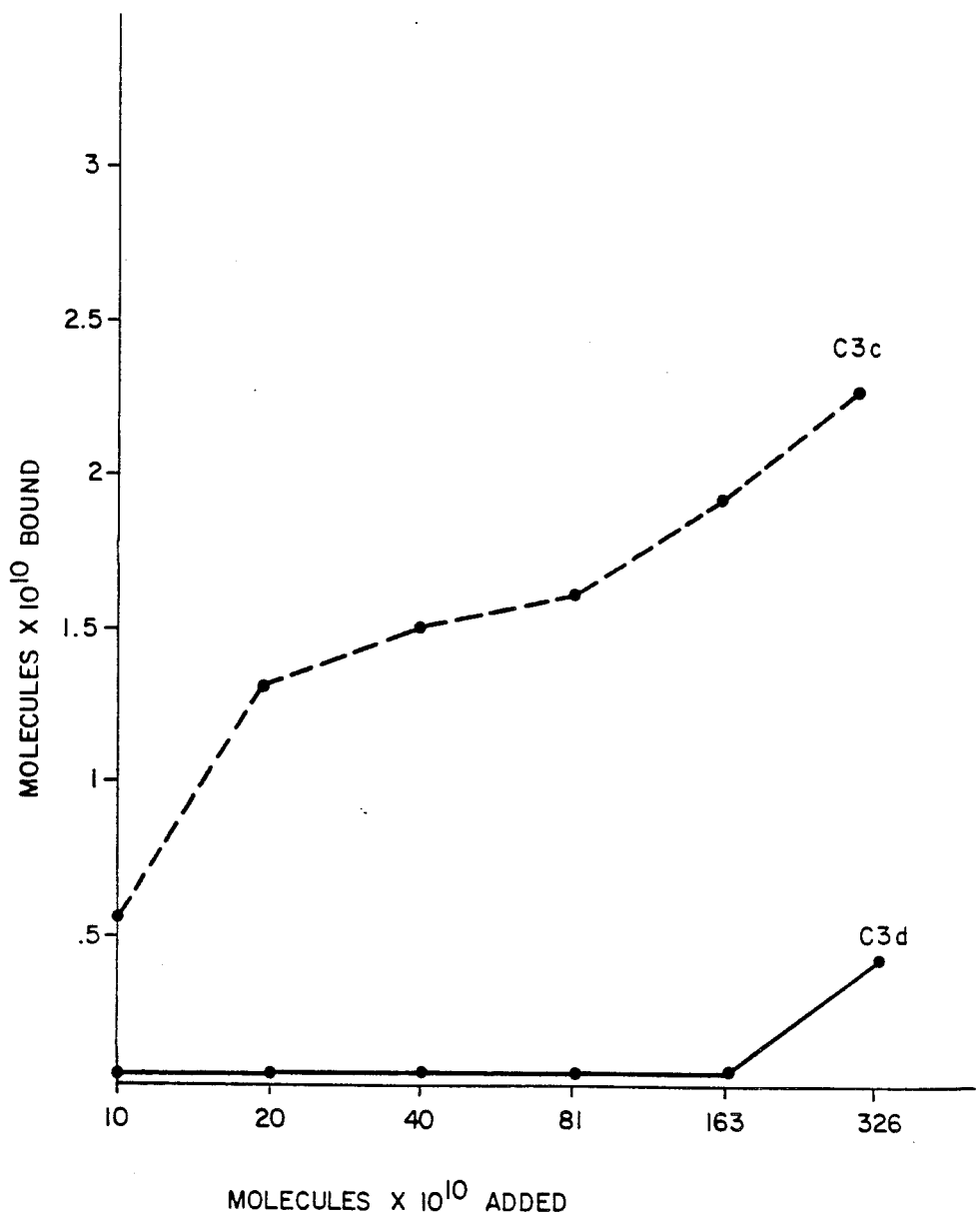
Figure 4:
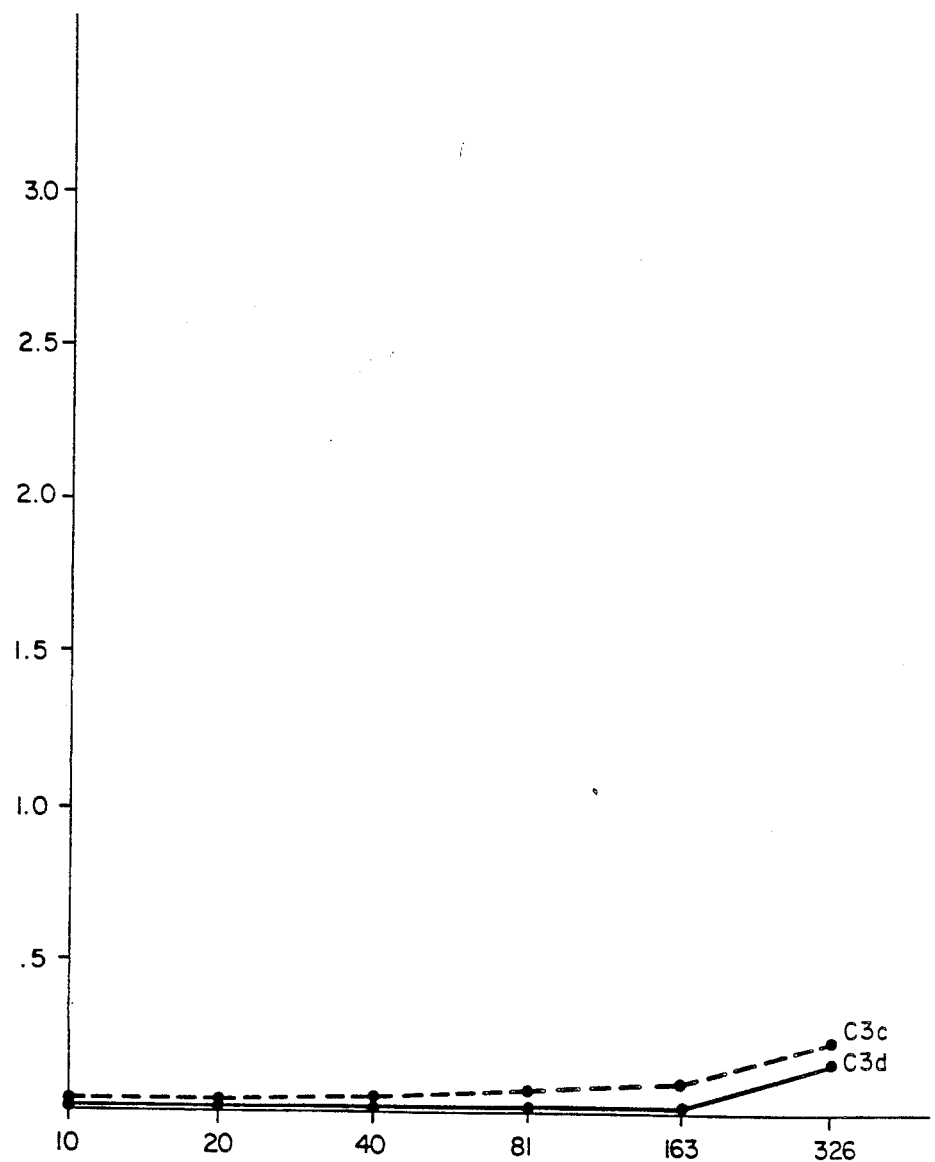
Figure 5:
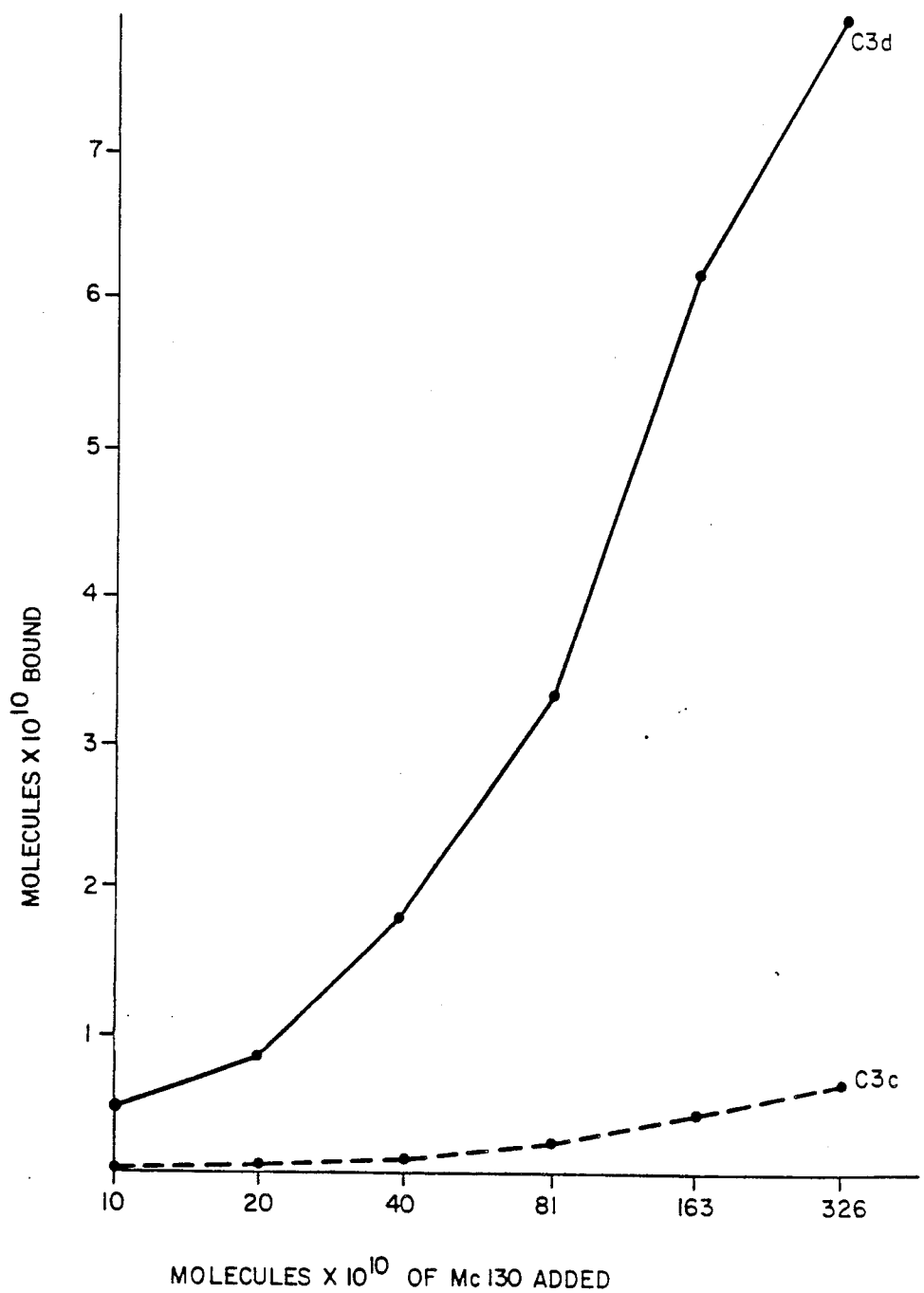
Figure 6:
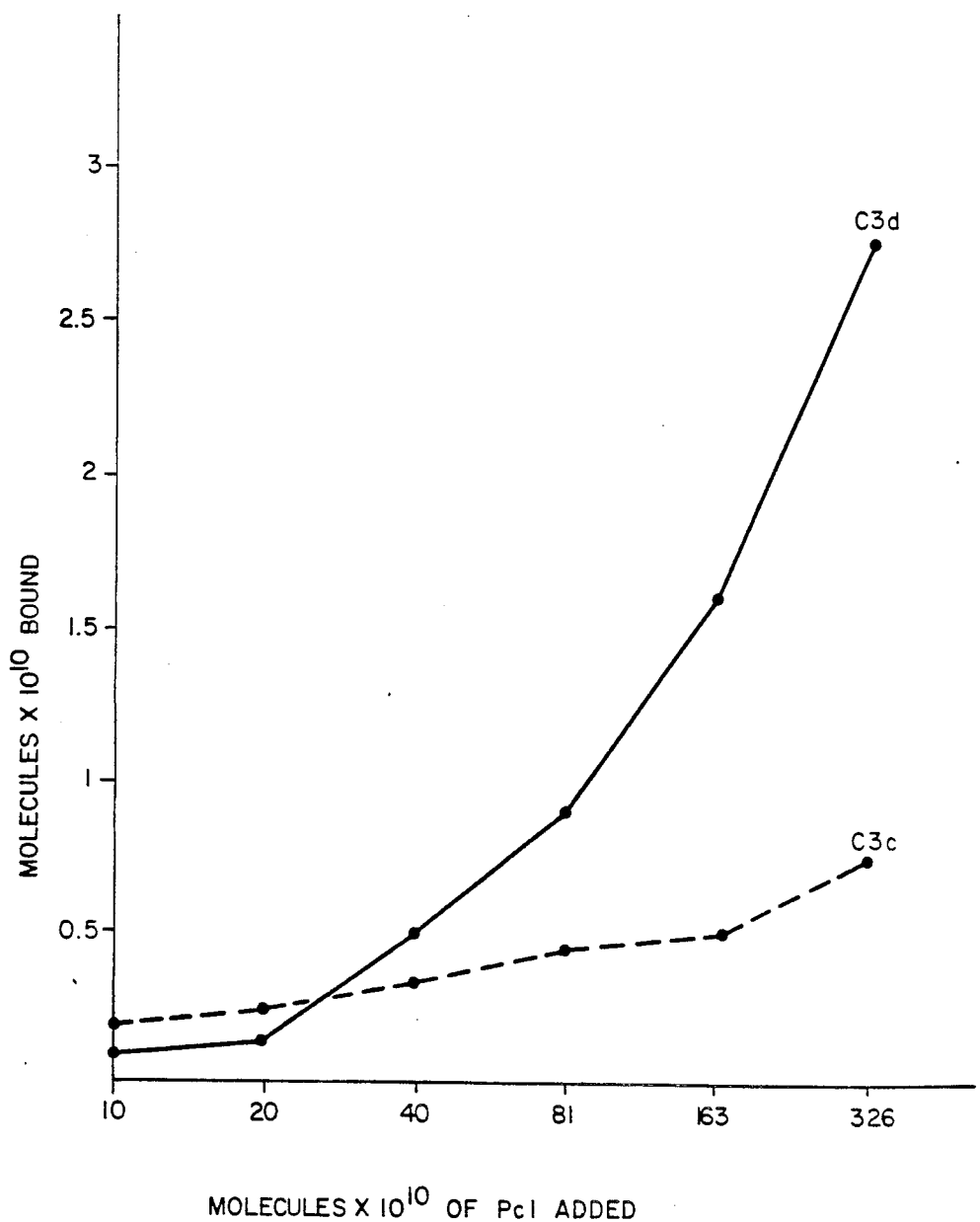
Figure 7:
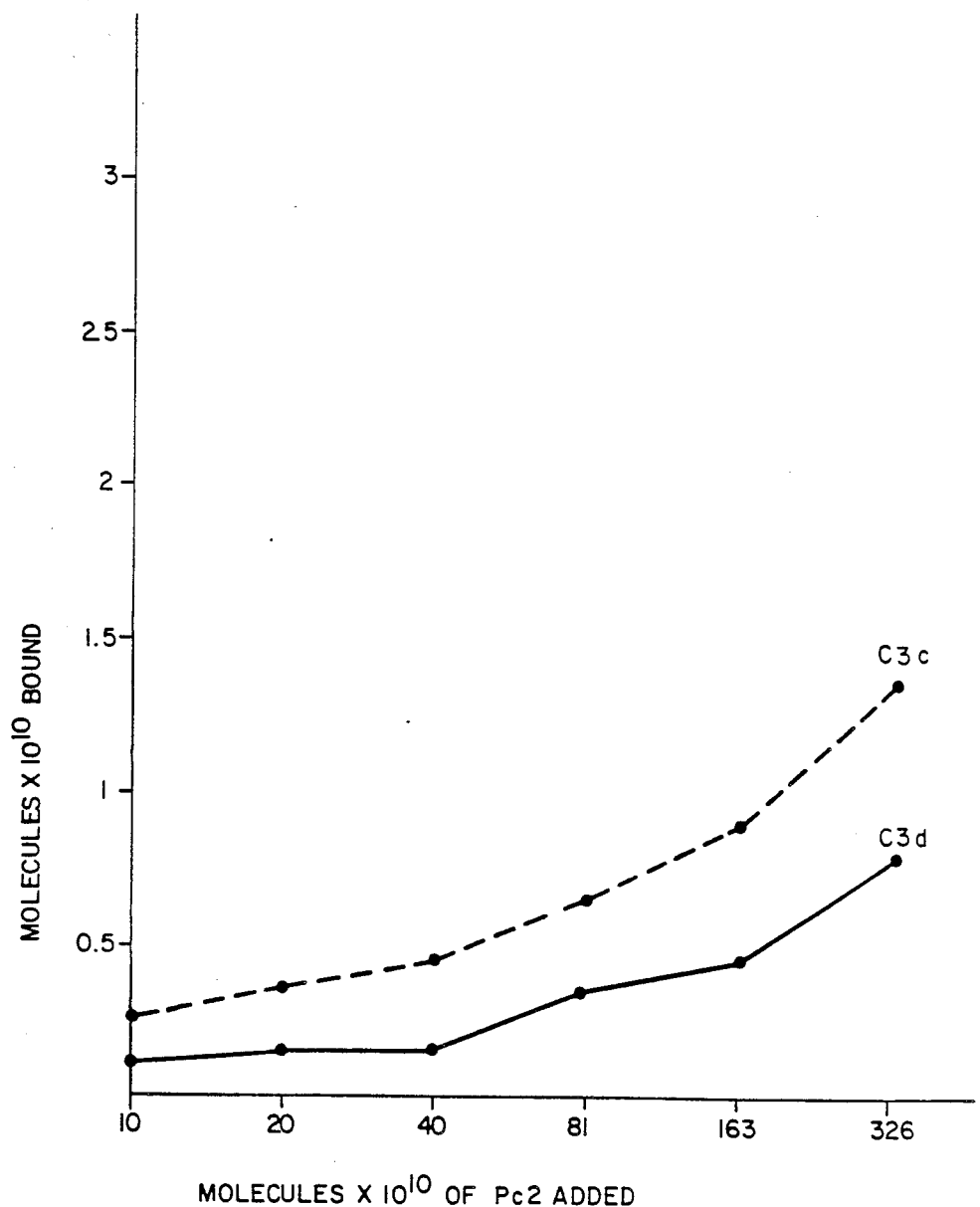

Therefore, polyclonal and monoclonal anti-C3 antibodies have been used to detect and subcategorize complement-fixing immune complexes and such antibodies are also used to detect C3 breakdown products that might signify complement system activation by immune complexes or other activating principals (i.e., bacteria lipopolysaccharide, viruses, etc.). Polyclonal antibodies have been made in goats, sheep or rabbits by using whole C3, C3d or the beta chain of the C3 molecule. Polyclonal antibodies against C3 recognize C3, C3b, iC3b, C3d and C3c. Antibodies against C3d recognize C3, C3b, iC3b and C3d, but not C3c. Antibodies against the beta chain of C3 (see configuration of C3 molecule in FIG. 1) recognize C3, C3b, iC3b and C3c but not C3d.

The monoclonal antibodies to be used and their reported specificities are given in Table I below. All have been made available to us by their developers. Monoclonal antibody 130 is secreted by the hybridoma designated MoAb 130, deposited with the American Type Culture Collection (ATCC) of Bethesda, Md. on Jan. 22, 1985 and having ATCC Accession Number HB 8702. One (#8) was given to us by R. Smith of Ortho Diagnostics and one (#7) was obtained from commercial sources (Bethesda Research Laboratories).

TABLE I

| | Derivation of Monoclonal Anti-C3 Antibodies | | | | |
|---|---|---|---|---|---|
| Monoclonal Antibody | Original Destination | Publication | Origin | IgG Subclass | Date Rec'd in Our Laboratory |
| 1 | 3 | Immunol 41: 503–515, 1980 | rat | IgG 2a* | 8/27/81 |
| 2 | 4 | | | IgG 2b* | |

TABLE I-continued

Derivation of Monoclonal Anti-C3 Antibodies

| Monoclonal Antibody | Original Destination | Publication | Origin | IgG Subclass | Date Rec'd in Our Laboratory |
|---|---|---|---|---|---|
| 3 | 9 | | | IgG 2b* | |
| 4 | 130 | J. Immunol. 128: 512–514, 1982 | mouse | IgG 2b/1* | 3/28/82 |
| 5 | 105 | J. Immunol. 129: 2024–2050, 1982 | mouse | IgG1 | |
| 6 | 111 | | mouse | IgG1 | |
| 7 | BRL | — | mouse | IgG 2b | 4/22/83 |
| 8 | ORTHO | — | mouse | IgG1* | 5/27/83 |

*As defined in our laboratory by double immunodiffusion against subclass specific antisera.

The detection and measurement of the presence of various C3 fragments and the subcategorizations of the human complex they are bound to can have useful clinical applications. The subcategorization of immune complexes according to the C3 fragment expressed is of particular importance for the following reasons:

(a) Immune complex-bound C3b is sequentially degraded by serum enzymes (factor I and factor H) and cellular CR1 (C3b receptors) into smaller fragments (4–8). Initially, immune complex-bound C3b is converted to iC3b, and then to C3dg or C3d, see FIG. 1. Thus, the type of C3 fragment on immune complexes varies depending on the rate of their formation and the state of the various inactivators of the complement system.

(b) The various immunocytes, phagocytes and other cell types (polymorphonuclear leukocytes, mast cells, eosinophils, red cells, platelets) that interact with complement-fixing immune complexes and free C3 fragments differ in their complement receptor profiles. (See Table II below.) As a result, one might expect that the degree of immune complex removal from the circulation and effects of immune complexes on immune and inflammatory processes would differ depending on the type of C3 fragments that predominate at a given time.

(c) Numerical defects in CR1 (C3b receptors) have been reported recently in patients with autoimmune diseases such as systemic lupus erythematosus (SLE). Since these receptors appear to play an important role in the degradation of immune complex-bound C3b, it would be reasonable to expect that the degree of CR1 receptor defect should correlate with types of immune complex-bound C3 fragments and with clinical outcome.

TABLE II

Receptors for C3 Fragments on Human Blood Cells

| Cell Type | C3a | CrI C3b–C4b | iC3b | C3d |
|---|---|---|---|---|
| Erythrocytes | — | + | −/+ | — |
| Platelets | — | — | — | — |
| Neutrophils | + | + | + | — |
| Macrophages | | | | |
| Monocytes | + | + | + | +? |
| Eosinophils | + | + | + | — |
| Basophil | | | | |
| Mast cells | + | ? | — | — |
| B lymphocytes | — | + | + | + |
| T lymphocytes | — | +? | — | — |

II. Determination of the Fine Specificity Of the Various Anti-C3 Antibodies.

Optimal amounts of antibodies are bound to wells of microtiter plates and incubated with varying amounts of radiolabeled C3 and its fragments (C3b, iC3b, C3d, C3dg, C3c). Uptake is determined and appropriate curves constructed. The reverse situation in which unlabeled C3 and its fragments are bound to wells and then reacted with radiolabeled polyclonal or monoclonal anti-C3 antibodies is employed. Monoclonals and polyclonals with specificity for C3c or C3d are identified, and immune complexes in pathologic sera can easily be subcategorized by following the mathematical equations given in Table III below.

TABLE III

Detection of IC by Monoclonal Antibodies of Different Subfragment Specificities

| Example | Specific for | Possible Activities Reactivities |
|---|---|---|
| Monoclonal 1 | C3d | C3b, C3bi, C3d,g |
| Monoclonal 2 | C3c | C3b, C3bi |
| Monoclonal 3 | C3g | C3bi, C3d,g |

For mathematical purposes the following assignment has been made:

$$C3b = n$$

$$C3bi = x$$

$$C3d,g = z$$

Following incubation of serum samples with the above solid-phase F(ab')$_2$ anti-C3 antibodies and subsequent detection of the bound IgG with radiolabeled or enzyme conjugated anti-IgG, the following equations and conclusions may be derived:

A = value with monoclonal 1 (n+x+z) - value with monoclonal 2 (n+x) should equal the proportion of immune complexes that express C3d,g (z)

B = value with monoclonal 1 (n+x+z) - value with monoclonal 3 (x+z) should equal the proportion of immune complexes that express C3b (n)

C = value with monoclonal 1 (n+x+z) - (A+B) should equal the proportion of immune complexes that express C3bi (x)

Monoclonal antibodies that recognize neoantigenic determinants expressed or activated can also be used. For this assay, wells of microtiter plates are coated, for example, with monoclonal anti-C3c neoantigen or C3d neoantigen antibodies (for example monoclonal 105 and monoclonal 130, respectively), reacted with a test sample, and then bound C3 fragments are detected with anti-C3 antibody. The coating reagent must discriminate between activated complement component and complement component in native or non activated stage.

The final reagent can be polyclonal anti-C3 or monoclonal anti-C3. The monoclonal may be directed against the same epitope (antigenic determinant) to that seen by the coating reagent or, preferably, against a different determinant so as to avoid competition for the binding site between the coating and final antibody. This final antibody can be radiolabeled or enzyme conjugated.

A reference curve may be constructed with known amounts of activated C3 or its fragments as middle reagents so as to express the results in terms of micrograms of activated C3 (made of biologic fluids). The test samples should be obtained in EDTA or any other inhibitor of complement activation so as to avoid false positive results caused by activation of complement in vitro during blood clotting.

Monoclonal anti-C3 antibodies which discriminate between immune complex bound C3 fragments and C3 fragments in solution can also be used to determine whether complement activation has been induced by immune complexes or other types of activators such as gram negative bacteria. In this system, complement activation is first assayed as above then the test sample is subjected to incubation with approximately 3 to 10 ml. polyethylene glycol (PEG) so as to precipitate out micromolecules such as immune complexes. Secondly, the supernatant is rechecked for presence of C3 fragments. There exist monoclonal anti-C3c neoantigen antibodies which do not bind efficiently activated C3 in fluid phase, but do they bind C3 fragments on immune complexes. Bovine conglutinin exhibits a similar trait with respect to iC3b.

III. Determination of the Available Monoclonal and Anti-C3 Antibodies Detect and/or Differentiate Immune Complex-Bound C3 Fragments vs. C3-Fragments Free in Solution.

Polyclonal or monoclonal anti-C3 antibodies are bound to wells of microtiter plates and then incubated with varying dilutions of the following: (a) serum, (b) plasma (blood to be collected in 0.01 M EDTA so as to chelate $CA^{++}$ and $Mg^{++}$ and inhibit complement activation by either the classical or alternative pathways), (c) serum whose complement has been activated by zymosan, inulin, or lipopolysaccharide, (d) serum whose complement has been activated by aggregated human gamma globulin or model complexes made in vitro, such as bovine serum albumin (BSA)-rabbit anti-BSA or tetanus toxoid-human antitetanus toxoid at various antigen:antibody ratios and e) serum treated first (37° C., 30 min) with gamma globulin aggregates or other model complexes and then incubated with polyethylene glycol (PEG) at a 3 percent final concentration. At this concentration, PEG precipitates high molecular weight materials such as immune complexes, but not low molecular weight materials such as monomeric IgG, free C3 or fragments thereof. Serum sample are tested before and after PEG precipitation.

Each of the above samples is incubated with the solid-phase-bound monoclonal $F(ab')_2$ anti-C3 antibodies (specific for C3c, C3d or neoantigens). Binding of immune complexes or C3 (and fragments) is then assessed with radiolabeled or enzyme conjugated $F(ab')_2$ polyclonal anti-IgG or polyclonal anti-human C3 antibody, respectively.

Monoclonal antibodies from five different sources have been examined for immune complex detection, C3 fragment specificity and ability to differentiate native C3 from activated C3. The original publications in which these antibodies were described, their designations, origins and IgG subclasses are given in Table I. The date on which these antibodies were first obtained and tested in our laboratory is also provided there.

FIGS. 2 through 7 show C3c and C3d specificities of most of the available monoclonal antibodies and of three polyclonal antibodies.

FIGS. 8 through 14 show the detection of immune complexes made in vitro (aggregated gamma globulin in human serum) by these antibodies.

FIGS. 15 through 22 show each of these antibodies reactivity with native C3 and activated C3 fragments bound to immune complexes or free in solution.

VI. Determination of the effects of CR1 (C3b receptor) on immune

Complex-bound C3 Fragments.

Aggregated human gamma globulin or other model immune complexes are mixed with (a) fresh human serum (source of complement) or (b) human serum plus human erythrocytes that express CR1 receptors. Following appropriate incubations, the materials are reacted with solid phase-bound $F(ab')_2$ anti-human C3c or anti-human C3d antibodies (polyclonal or monoclonal). Subsequently, bound complexes are detected with radiolabeled or enzyme-linked anti-human IgG (or protein A if the anti-C3 antibodies are used as $F(ab')_2$. In the presence of serum alone, the immune complexes bear primarily C3b or iC3b, whereas in the presence of serum and CR1, the complexes carry primarily C3d,g or C3d. Thus, a value of immune complexes registered with anti-C3c antibodies (reacting with C3b bearing complexes) as the primary reagent is lower in the case of immune complexes + serum + CR1 than in the case of immune complex + serum.

V. Determination of whether the anti-C3 assay For immune complexes can be reversed to

Exemplify its possible commercial usage.

Microtiter wells are coated with polyclonal $F(ab')_2$ anti-human IgG or staphylococcal protein A, which has specifically for the Fc portion of all human IgG subclasses. Washed wells are incubated with serum samples or complexes made in vitro in serum and finally with radiolableed or enzyme-conjugated $F(ab')_2$ anti-human C3 polyclonal or monoclonal antibodies.

Table IV shows the results with complexes made in vritro after reversing the order of the anti-C3 assay. Anti-IgG or protein A is the primary solid-phase bound reagent, test serum with aggregated gamma globulin is middle reagent, and labeled monoclonal or polyclonal anti-C3 antibodies is the final reagent.

TABLE IV

| The Reverse Anti-C3 Assay for Immune Complexes | | | | | | | | | | | | |
|---|---|---|---|---|---|---|---|---|---|---|---|---|
| AHG | MC 130 | | | MC 3 | | | MC 4 | | | Polyclonal anti-C3 | | |
| g/ml | 1600 | 800 | 400 | 1600 | 800 | 400 | 1600 | 800 | 400 | 1600 | 800 | 400 |
| anti-human | 20 | 4.14 | 3.76 | 1.14 | 6.86 | 4.88 | 2.66 | 13.05 | 7.27 | 2.98 | 44.95 | 29.64 | 15.15 |
| IgG | 10 | 4.63 | 3.41 | 1.84 | 6.71 | 3.53 | 1.59 | 14.40 | 8.90 | 4.15 | 43.75 | 28.98 | 15.06 |
| in the | 5 | 4.93 | 2.48 | 1.31 | 6.28 | 2.69 | 1.45 | 10.45 | 6.34 | 3.30 | 45.18 | 28.66 | 15.09 |
| plate | 1 | 1.47 | 1.40 | 0.43 | 1.85 | 0.55 | 0.56 | 3.92 | 2.31 | 1.24 | 12.93 | 9.55 | 6.30 |

TABLE IV-continued

| | | | | | | The Reverse Anti-C3 Assay for Immune Complexes | | | | | | | |
|---|---|---|---|---|---|---|---|---|---|---|---|---|---|
| SPA | 20 | 4.21 | 1.67 | 1.24 | 3.31 | 0.61 | 0.41 | 7.41 | 3.86 | 1.87 | 20.26 | 15.22 | 7.78 |
| in the | 10 | 2.21 | 0.92 | 0.85 | 2.08 | 1.11 | 0.58 | 4.46 | 2.75 | 1.26 | 17.21 | 10.64 | 7.43 |
| plate | 5 | 2.95 | 1.91 | 0.72 | 2.80 | 0.96 | 0.41 | 5.76 | 3.18 | 1.47 | 14.12 | 10.25 | 5.60 |
| | 1 | 3.60 | 2.16 | 0.70 | 2.12 | 0.84 | 0.32 | 4.89 | 2.30 | 0.55 | 12.28 | 9.50 | 5.35 | g/ AHF/ml serum
Results expressed as g uptake
*Microtiter wells were coated with various amounts of F(ab')$_2$ anti-human IgG or SPA (20, 10, 5, 1 g/ml). Washed wells were incubated with various amounts of aggregated human gamma globulin (AHG; 1600, 800, 400 g/ml) in human serum and then reacted with radiolabeled monoclonal or polyclonal anti-C3 antibodies (ELISA assays can also be used).

VII. Determination of the incidence and types of C-fixing immune complexes in pathologic sera.

Microtiter wells are coated with polyclonal or monoclonal antibodies specific for C3c (which will react with C3b, iC3b, C3c) or C3d (which will react with C3b, iC3b, C3d), then incubated with the serum or plasma samples appropriately diluted and finally with radiolabeled or enzyme-conjugated F(ab')$_2$ anti-human IgG.

To avoid interference by rheumatoid factors, the anti-C3 polyclonal or monoclonal antibodies are preferably used as F(ab')$_2$ portions. When whole antibodies are used, the test samples are diluted in buffers containing the IgG of the species from which the antisera were derived (for mouse and rat monoclonals use mouse or rat IgG, respectively, of the same subclass as that of the monoclonals). Such IgGs may need aggregation by heating (usually 63° C. for 30 min) before mixing with the diluent buffer, since rheumatoid factors are known to react well with aggregated IgG but very poorly with monomeric IgG.

By subtracting the value obtained with the anti-C3d antibody from that yielded by the anti-C3c antibody, the proportion of immune complexes which contain C3b and C3d can be determined. The results are compared for samples representing several diseases and different stages of a given disease (active, inactive, associated clinical and pathologic features). The results also are correlated with those obtained with other immune complex assay systems such as the Raji cell assay (Raji cells express C3d receptors), the human red blood cell assay (red cells express only C3b receptors) and the conglutinin assay (conglutinin binds to iC3b only).

Tables V and VI below show the immune complex levels detected with monoclonal and polyclonal anti-C3 antibodies in plasmas of patients with SLE or rheumatoid arthritis (RA) and of normal controls.

TABLE VI

| Immune Complex Levels in SLE (microgram AHG equivalent/ml) | | | | | |
|---|---|---|---|---|---|
| Diagnosis Polyclonal Diagnosis | Monoclonal 105 | Monoclonal 130 | Polyclonal Ced | Monoclonal 130 | Polyclonal to C3d |
| SLE | 1.2 | 1.5 | 6.6 | 2.2 | 3.7 |
| SLE | 0.9 | 1.5 | 1.8 | 0.7 | 3.8 |
| SLE | 1.2 | 0.7 | 1.9 | 1.1 | 1.0 |
| SLE | 1.1 | 0.7 | 1.5 | 0.7 | 0.9 |
| SLE | 3.6 | 3.9 | 2.4 | 2.7 | 1.8 |
| RA | 4.4 | 0.7 | 63.0 | 19.5 | 75.0 |
| SLE | 0.8 | 0.7 | 4.5 | 1.3 | 1.3 |
| SLE | 1.8 | 0.7 | 2.3 | 0.7 | 29.0 |
| RA | 1.9 | 1.5 | 1.7 | 0.7 | 10.5 |
| RA | 0.9 | 0.7 | 2.2 | 0.7 | 12.5 |
| SLE | 1.2 | 0.7 | 0.7 | 1.3 | 0.8 |
| RA | 3.1 | 0.7 | 3.7 | 3.1 | 31.5 |
| SLE | 0.9 | 0.7 | 2.3 | 0.7 | 1.5 |
| RA | 1.5 | 1.5 | 25.0 | 0.7 | 31.0 |
| RA | 8.4 | 0.7 | 30.0 | 3.6 | 400.0 |
| SLE | 0.9 | 0.7 | 2.8 | 1.5 | 0.9 |
| SLE | 0.9 | 0.7 | 6.8 | 1.5 | 0.9 |
| SLE | 1.2 | 0.7 | 1.9 | 0.7 | 3.9 |
| SLE | 1.8 | 1.7 | 3.5 | 2.5 | 12.0 |
| RA | 5.2 | 5.8 | 3.3 | 4.0 | 8.2 |
| SLE | 1.5 | 1.8 | 2.0 | 0.7 | 2.0 |
| SLE | 2.0 | 2.5 | 2.0 | 0.7 | 0.7 |
| SLE | 0.8 | 0.7 | 0.7 | 0.8 | 0.7 |
| SLE | 2.5 | 2.6 | 5.0 | 3.5 | 2.7 |
| SLE | 0.8 | 0.7 | 2.3 | 1.1 | 1.3 |
| RA | 2.9 | 0.7 | 1.2 | 7.4 | 30.5 |
| SLE | 1.2 | 0.7 | 2.0 | 0.7 | 0.8 |
| SLE | 1.2 | 0.7 | 15.0 | 0.7 | 0.7 |
| SLE | 0.8 | 0.7 | 1.6 | 0.7 | 1.2 |

TABLE V

| Immune Complex Levels in SLE and RA by the Anti-C3 Assay Immune Complex Levels (microgram AHG equivalent/ml) | | | |
|---|---|---|---|
| Diagnosis | Monoclonal 105 | Monoclonal 130 | Polyclonal to C3d |
| SLE | 2.0 | 1.5 | 25.0 |
| SLE | 1.0 | 2.0 | 2.0 |
| SLE | 1.0 | 1.0 | 14.0 |
| RA | 2.0 | 2.5 | 66.0 |
| SLE | 1.0 | 1.0 | 3.0 |
| RA | 1.0 | 1.0 | 11.0 |
| SLE | 1.0 | 2.5 | 10.0 |
| SLE? | 1.0 | 6.0 | 12.0 |
| SLE? | 1.0 | 1.0 | 3.0 |
| SLE? | 1.0 | 7.0 | 3.0 |
| SLE? | 1.0 | 1.0 | 6.0 |
| SLE? | 1.0 | 1.0 | 6.0 |
| RA | 54.0 | 18.0 | 17.0 |

TABLE V-continued

Immune Complex Levels in SLE and RA by the Anti-C3 Assay
Immune Complex Levels (microgram AHG equivalent/ml)

| Diagnosis | Monoclonal | Monoclonal | Polyclonal |
|---|---|---|---|
| SLE | 1.0 | 1.0 | 19.0 |
| SLE | 1.0 | 1.0 | 6.0 |
| RA | 1.5 | 9.0 | 15.0 |
| RA | 2.0 | 100.0 | 110.0 |
| SLE | 2.0 | 1.0 | 22.0 |
| SLE? | 1.0 | 1.0 | 6.0 |
| SLE | 1.0 | 3.0 | 3.0 |
| SLE | 1.0 | 2.0 | 4.0 |
| SLE | 2.5 | 24.0 | 15.0 |
| SLE? | 1.0 | 1.0 | 6.0 |
| SLE | 1.0 | 2.5 | 6.0 |
| SLE | 1.0 | 2.5 | 10.0 |
| SLE | 1.0 | 2.0 | 3.0 |
| SLE | 1.0 | 2.5 | 15.0 |
| RA | 1.0 | 1.0 | 6.3 |
| SLE | 1.0 | 1.0 | 3.0 |
| RA | 1.0 | 2.0 | 3.0 |
| SLE | 3.5 | 7.0 | 33.0 |
| RA | 1.5 | 5.5 | 3.0 |
| SLE | 2.0 | 34.0 | 25.0 |
| SLE | 3.5 | 6.0 | 78.0 |

The advantages of this method and system include the following:

1. Exquisite specificity for detection of complement-fixing immune complexes.

2. Subcategorization of immune complexes according to the state of C3 that they express. This facilitates correlation of immune complex concentrations with disease states and clinical status and, indirectly, detection of defects in CR1 and other serum factors that normally convert C3b to C3d.

3. Detection of complement system activation without the use of cumbersome hemolytic assays or insensitive immunodiffusion assays, and perhaps definition of the source responsible for such activation (Immune complexes vs. bacteria or viruses vs. LPS-like substances).

Numerous publications have clearly established the important role of immune complexes in the pathogenesis of immunologically mediated diseases, including autoimmune diseases and neoplasia. Although existing techniques are widely used, interpretation of their results is subject to considerable confusion because all of them are beset by the lack of absolute specificity. Thus, the medical community awaits with great anticipation a technique that will be simple and specific as, we believe, the anti-C3 assay is. The potential usages of such a technique are enormous.

The specificity studies performed with the battery of monoclonal and polyclonal antibodies employed show that: (a) Some of them (monoclonals 3, 130 and polyclonal 1, 2) react with an antigenic determinant on the C3d fragment and some (monoclonals 4 and polyclonal 1, 2) with an antigenic determinant on the C3c fragment. (b) Some of them (monoclonals 3, 130, 105, 111) recognize neoantigenic determinants (bind C3 fragments but do not react with the native molecule of C3). (c) Some show better binding with immune complex-fixed C3 fragments (monoclonals 105, 111) than with free C3 fragments (monoclonals 3, 4, 130, BRL, and polyclonal #1) generated by complement activation.

Most of the monoclonal antibodies tested are efficient detectors of model immune complexes formed in vitro (aggregated human gamma globulin + complement).

Despite the efficient detection of model immune complexes, monoclonal antibodies registered lower value and incidence than polyclonal antibodies when plasmas from patients with immune complex associated diseases (SLE, RA) were studied.

The values with polyclonal anti-C3d and anti-C3c antibodies in most instances were not parallel. The majority of plasmas showed higher values with anti-C3d than anti-C3c, indicating that immune complex-bound C3b-iC3b is converted in vitro to C3d by the action of FActor I, FActor H, CR1 and other proteolytic enzymes. However, in a few instances, both types of polyclonal antibodies registered similar values, indicating that the immune complexes we detected expressed C3b or iC3b.

BIBLIOGRAPHY

1. A.N. Theopfilopoulos, F.J. Dixon. In: Advances in Immunology 28:89–220, 1979. (F.J. Dixon and M.G. Kunkel, Eds). Academic Press, N.Y.

2. J.M. Weiler, et al. Immunol. Today 3:238–242, 1982.

3. A.B. Pereith, A.N. Theofilopoulos, F.J. Dixon. J. Immunol. 125:763–770, 1980.

4. Fearon. Proc. Natl. Acad. Sci. U.S.A. 79:5867–5871, 1982.

5. Medof, Prince, Mold. Proc. Natl. Acad. Sci. U.S.A. 79:5047–5051, 1982.

6. Ross. Fed. Proc. 41:3089–3093, 1982.

7. Ross, Lambris, Cain, Newman. J. Immunol. 129:2051–2060, 1982.

8. Medof, Iida, Mold, Nussenzweig. J. Exp. Med. 156:1739–1754, 1982.

9. Miyakawa, Yamada, Kosaka, Tsuda, Kosugi, Mayumi. Lancet 493–497, Sept. 1981.

10. Iida, Mornaghi, Nussenzweig. J. Exp. Med. 155:1427–1438, 1982.

11. Wilson, Wong, Schur, Fearon. N. Eng. J. Med. 307:981–986, 1982.

12. Lachman, Oldroyd, Milstein, Wright. Immunol. 41:503–515, 1980.

13. Burger, Deubel, Hadding, Bitter-Suermann. J. Immunol. 129:2041–2050, 1982.

14. Tamerius, Pangburn, Muller-Eberhard. J. Immunol. 128:512 514, 1982. 10 15. Geides, Naiem, Mason, Stein. Immunol. 45:645–653, 1982.

16. Creighton, Lambert, Miescher. J. Immunol. 111:1219–1227, 1976.

17. J.J. Langone. In: Advances in Immunology 32:157–252, 1982. (F.J. Dixon and H.G. Kunkel, Eds.) Academic Press, N.Y.

18. Van Snick, Stassin, de Lestre. J. Exp. Med. 157:1006–1019, 1983.

19. Lambris, Dobson, Ross. Proc. Natl. Acad. Sci. U.S.A. 78:1828–1832, 1981.

20. Tsuda, Miyakawa, Mayumi. Immunol. 37:681–688, 1979.

21. Casali, Bossus, Carpentier, Lambert. Clin. Exp. Immunol. 29:342–354, 1977.

22. Eisenberg, Theofilopoulos, Dixon. J. Immunol. 118:1428, 1977.

23. Linscott W.D., Ranken R., Triglia R.P. J. Immunol. 121:658, 1978.

What is claimed is:

1. A method of determining the fragments of a complement component in a sample comprising the steps of:
   (a) binding a plurality of specific binding agents to the complement component fragments in the sample, each binding agent being specific to a different fragment of the complement component;

(b) measuring the amount of binding by each specific binding agent to its respective fragments to obtain a value for each agent;

(c) correlating the values determined in step (b) from which is calculated a value for the amount of a particular complement component fragment present in the sample, the particular fragment being other than those fragments corresponding to the specific binding agents.

2. The method of claim 26 wherein the sample is divided into parts, each part being subjected to a different specific binding agent.

3. The method of claim 2 wherein the parts are of equal volume.

4. The method of claim 1 wherein the specific binding agents are antibodies.

5. The method of claim 1 wherein the amount of each specific binding agent bound to immune complexes is measured.

6. The method of claim 1 wherein at least one of the specific binding agents comprises an idiotype-containing polyamide portion of an antibody.

7. The method of claim 1 wherein the complement component is C3 and the fragments are C3 fragments.

8. The method of claim 1 wherein at least one of the binding agents comprises at least the idiotype-containing polyamide portion of a monoclonal antibody.

9. The method of claim 8 wherein the monoclonal antibody is to a neoantigen of a complement component fragment.

10. A method of determining the C3 fragments bound to immune complexes in a sample comprising the steps of:

(a) binding a plurality of specific binding agents to C3 fragments in the sample, each binding agent being specific to a different C3 fragment;

(b) measuring the amount of binding by each specific binding agent to its respective C3 fragments bound to immune complexes to obtain a binding value for each agent;

(c) correlating the values determined in step (b) from which is calculated a value for the amount of a particular C3 fragment bound to immune complexes present in the sample that is other than those C3 fragments corresponding to the specific binding agents.

11. The method of claim 10 wherein the specific binding agents are antibodies.

12. The method of claim 10 wherein at least one of the specific binding agents comprises an idiotype-containing polyamide portion of an antibody.

13. The method of claim 10 wherein at least one of the binding agents comprises at least the idiotype-containing polyamide portion of a monoclonal antibody.

14. The method of claim 13 wherein the monoclonal antibody is to a neoantigen of a complement component fragment.

15. An assay system for determining the amount of C3d,g bound to an immune complex in a sample comprising in kit form:

(a) a first binding agent specific for a C3d fragment bound to an immune complex;

(b) first means for measuring the amount of first specific binding agent bound to said C3d fragment which is bound to an immune complex;

(c) a second binding agent specific for a C3c fragment bound to an immune complex; and (d) second means for measuring the amount of second specific binding agent bound to said C3c fragment which is bound to an immune complex.

16. The assay system of claim 15 wherein at least one of the specific binding agents comprises an idiotype-containing polyamide portion of an antibody.

17. The assay system of claim 15 further including means for comparing the value obtained from the first means for measuring with the value obtained by the second means for measuring.

18. A method of determining the amount of C3d,g bound to immune complexes in a sample, comprising the steps of:

(a) binding a first specific binding agent for C3d to any complement component fragments which include the C3d moiety present in at least a portion of the sample;

(b) measuring the amount of binding by the first specific binding agent to C3d bound to immune complexes to obtain a first value;

(c) binding a second specific binding agent for C3c to any complement component fragments which include the C3c moiety present in at least a portion of the sample to obtain a second value;

(d) measuring the amount of binding by the second specific binding agent to C3c bound to immune complexes to obtain a second value; and (e) subtracting the second value from the first value to obtain a value indicating the amount of C3d,g bound to immune complexes present in the sample.

19. A method of determining the amount of C3b bound to immune complexes in a sample, comprising the steps of:

(a) binding a first specific binding agent for C3d to any complement component fragments which include the C3d moiety present in at least a portion of the sample;

(b) measuring the amount of binding by the first specific binding agent to C3d bound to immune complexes to obtain a first value;

(c) binding a second specific binding agent for C3g to any complement component fragments which include the C3g moiety present in at least a portion of the sample;

(d) measuring the amount of binding by the second specific binding agent to C3g bound to immune complexes to obtain a second value; and (e) subtracting the second value from the first value to obtain a value indicating the amount of C3b bound to immune complexes present in the sample.

20. A method of determining the amount of iC3b bound to immune complexes in a sample, comprising the steps of:

(a) binding a first specific binding agent for C3d to any complement component fragments which include the C3d moiety present in at least a portion of the sample;

(b) measuring the amount of binding by the first specific binding agent to C3d bound to immune complexes to obtain a first value;

(c) binding a second specific binding agent for C3c to any complement component fragments which include the C3c moiety present in at least a portion of the sample;

(d) measuring the amount of binding by the second specific binding agent to C3c bound to immune complexes to obtain a second value;

(e) binding a third specific binding agent for C3g to any complement component fragments which include the C3g moiety present in at least a portion of the sample;

(f) measuring the amount of binding by the third specific binding agent to C3g bound to immune complexes to obtain a third value; and (g) subtracting the first value from the sum of the second and third values to obtain a value indicating the amount of iC3b bound to immune complexes present in the sample.

21. A diagnostic assay system for determining the type and amount of a particular C3 complement component fragment bound to a complement-fixing antibody-containing immune complex, the system comprising in kit form:

(a) a first specific binding agent specific to either a complement component fragment C3d or C3c antigen or to the antibody component of the immune complex; and (b) a second specific binding agent specific to the other of the complement component fragment C3d or C3c antigen or the antibody component of the immune complex, the second specific binding agent including a label; when contacted with the complement-fixing immune complex in the sample to be assayed, the first and second specific binding agents individually binding to and forming an aggregate with the complement-fixing immune complex, such that the aggregate so formed is separable from any second specific binding agent that is not part of the aggregate.

22. The assay system of claim 21 further including a solid matrix on which the first specific binding agent can be immobilized.

23. The assay system of claim 21 wherein at least one of the specific binding agents comprises an idiotype-containing polyamide portion of an antibody.

24. The assay system of claim 21 wherein the first binding agent is specific to a C3d or C3c antigen and the second binding agent is specific to the antibody component of the immune complex.

25. The assay system of claim 21 wherein at least the first specific binding agent comprises at least the idiotype-containing polyamide portion of a monoclonal antibody.

26. The assay system of claim 25 wherein the monoclonal antibody is to a neoantigen of a C3d or C3c complement component fragment.

27. A method of determining the amount of fluid phase and immune complex-bound C3 fragments in a sample, comprising the steps of:

(a) determining the amount of a particular C3 fragment in a first portion of the sample by binding that fragment with a specific binding agent to obtain a first value;

(b) removing immune complexes from a second portion of the sample;

(c) determining the amount of the particular C3 fragment present in the second portion after the immune complexes are removed to obtain a second value; and (d) comparing the first and second values.

28. The method of claim 27 wherein the immune complexes are removed by precipitation.

* * * * *